US006458798B1

(12) United States Patent
Fujita et al.

(10) Patent No.: US 6,458,798 B1
(45) Date of Patent: Oct. 1, 2002

(54) BICYCLIC PYRIMIDINE COMPOUNDS AND THERAPEUTIC USE THEREOF

(75) Inventors: Hitoshi Fujita, Takatsuki; Fujio Antoku, Nishinomiya; Norio Fujiwara, Yao; Kiyotaka Iwai, Toyonaka; Hiroshi Tanaka, Tokyo-to; Hajime Kawakami, Nishinomiya, all of (JP)

(73) Assignee: Sumitomo Pharmaceuticals Company, Limited, Osaka (JP)

( * ) Notice: Subject to any disclaimer, the term of this patent is extended or adjusted under 35 U.S.C. 154(b) by 0 days.

(21) Appl. No.: 09/763,728

(22) PCT Filed: Aug. 20, 1999

(86) PCT No.: PCT/JP99/04505

§ 371 (c)(1),
(2), (4) Date: Feb. 27, 2001

(87) PCT Pub. No.: WO00/12487

PCT Pub. Date: Mar. 9, 2000

(30) Foreign Application Priority Data

Aug. 27, 1998 (JP) ............................................. 10-241842
Sep. 8, 1998 (JP) ............................................. 10-253506

(51) Int. Cl.⁷ .................. C07D 239/95; C07D 491/052; A61K 31/517; A61K 31/519
(52) U.S. Cl. .............................. 514/260.1; 514/266.4; 544/278; 544/291
(58) Field of Search ................................ 544/278, 291; 514/258, 260, 260.1, 266.4

(56) References Cited

U.S. PATENT DOCUMENTS 3,185,691 A    5/1965   Pribyl et al. ............. 260/256.4
3,272,811 A    9/1966   Ohnacker et al. ........ 260/247.1

FOREIGN PATENT DOCUMENTS

GB      A1152883      5/1969
JP      A2-4235976    8/1992
WO      WO 97/09325   3/1997

OTHER PUBLICATIONS

Modest et al., Chemical Abstract 63:5639f, 1965.*
Ross et al., Chemical Abstract 54:6742b, 1960.*
Elslager et al., Journal of Medicinal Chemistry, vol. 17, No. 1, pp. 75–100 (1974).

* cited by examiner

*Primary Examiner*—Richard L. Raymond
*Assistant Examiner*—Deepak Rao
(74) *Attorney, Agent, or Firm*—Birch, Stewart, Kolasch & Birch, LLP

(57) ABSTRACT

A pyrimidine derivative of the formula (1) or a salt thereof;

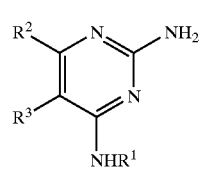

(1)

has an inhibitory activity of production of Th2 type cytokines such as IL-4, IL-5, etc., and is useful as an therapeutic agent for allergic diseases, autoimmune diseases such as systemic lupus erythemathosus, etc., and acquired immunodeficiecy syndrome (AIDS) and so on.

13 Claims, No Drawings

BICYCLIC PYRIMIDINE COMPOUNDS AND THERAPEUTIC USE THEREOF

This application is the national phase under 35 U.S.C. § 371 of PCT International Application No. PCT/JP99/04505 which has an International filing date of Aug. 20, 1999, published in japanese which designated the United States of America.

TECHNICAL FIELD

The present invention relates to pyrimidine derivatives and medicinal uses thereof. In more detail the present invention relates to pyrimidine derivatives having activities for suppression of type 2 helper T cell (Th2) immune responses and enhancement of type 1 helper T cell (Th1) immune responses and therapeutic methods for immune diseases by using the pyrimidine derivatives and therapeutic compositions containing the pyrimidine derivatives.

BACKGROUND ART

It is first proposed by Mosmann et al. that Lymphocytes, called helper T cells which play the central role in immune responses are classified into two subsets. They classified mouse helper T cells (Th) into Th1 and Th2 depending on the kinds of cytokines produced (J. Immunol. 136, 2348–2357 (1986)).

As Th1-type cytokines, interleukin 2 (IL-2), interferon γ (IFN-γ), etc. are illustrated. As Th2-type cytokines, interleukin 4 (IL-4), interleukin 5 (IL-5), interleukin 10 (IL-10), interleukin 13 (IL-13), etc. are illustrated.

Nowadays thinking of the classification into Th1/Th2 is applied to the classification of helper T cell subsets, and also regarding a variety of immune responses in the living body on the point of view of which subset of helper T cells mainly participates, the immune responses have become to be interpreted "immune responses on Thl-type" or "immune responses on Th2-type", respectively.

Immune responses on Th1-type are mainly induced by cytokines such as interleukin 2 (IL-2), interferon γ (IFN-γ), etc. produced by activated Th1. Thus, it is known that Th1 cytokines participate to cell-mediated immunity such as protection mainly against infections of virus, bacteria, etc. by activation of macrophage, natural killer cells etc., or by further activation of Th1 via IL-12 etc. produced by the activated macrophages.

On the other hand, immune responses on Th2-type are mainly induced by cytokines such as IL-4, IL-5, etc. produced by activated Th2. Thus, it is known that Th2 cytokines participate to humoral immunity such as production of antibodies (e.g. IgE class) from B cells.

Since Th2 produce cytokines such as IL-4 or IL-5 which relates to allergic reaction, as mentioned below, Th2 are suggested to be the responsible cells on allergic reaction. For example, IL-4, a typical Th2-type cytokine, intduces production of IgE antibodies from B cells. IL-4 also induces expression of VCAM-1 gene, which is an important molecule which works when eosinophils adhere to vascular endothelial cells and infiltrate into the tissue (Farumashia, 29, 1123–1128(1993)). Recently IL-4 has been paid attention as a differentiation-inducing factor for Th2. IL-5, another Th2-type cytokine, induces differentiation, migration and activation of eosinophils. Allergic inflammation is characterized in being triggered off by infiltration, activation and degranulation of eosinophils, as typical chronic airway inflammation in asthma. Thus IL-5 is considered to be a factor inducing allergic inflammation.

Since Th2 cytokines have above properties, it is recognized that Th2 control both allergic reactions of "early phase reaction" by IgE antibodies or mast cells and "late phase reaction" by eosinophils, and therefore, Th2 are central cells in allergic inflammation. And it is considered that allergic diseases are caused by over expression of Th2-type immune responses. This consideration is also supported by findings of presence of Th2 or production of Th2-type cytokines such as IL-4, IL-5, etc. in the lesion of allergic disease, such as airway or skin.

Therefore, it is considered to be important to suppress immune responses of Th2, in order to inhibit both ealy phase and late phase reactions, or inhibit allergic inflammatory reaction characterized with infiltration and activation of eosinophils in the stage of fundamental source and to treat therapeutically and prophylactically general allergic diseases. Namely, if a drug is developed to suppress immune responses of Th2-type, the drug will be one for therapeutic and prophylactic agent for allergic diseases.

In especially serious chronic asthma or atopic dermatitis among allergic diseases, late phase reaction is considered to play an important role. However, anti-allergic agents used nowadays are mainly based on anti-histamine activity and inhibit only early phase reaction and clinical effect thereof is not satisfactory. From such viewpoints too, it has been desired to develop the drug which inhibits both early phase and late phase reactions by suppressing immune responses of Th2 and treats therapeutically and prophylactically for general allergic diseases as mentioned above.

Moreover, bronchodilators, which are represented by xanthine derivatives or β-stimulants which have been used as asthma agents for long years, are known to have suppressive activity of constriction of broncho smooth muscle by various stimulation. However, these are ineffective to chronic airway inflammation which is a basic cause for asthma. In addition, side effects of xanthine derivatives or β-stimulants to circulatory organs are anxious. In recent asthma therapy, as definitely shown in the guide line of WHO, asthma is taken as chronic inflammation of airway and it has made a principal object to cure the chronic inflammation of air way. The chronic inflammation of airway in asthma is triggered off by infiltration, activation and degranulation of eosinophils and has its pathologic characteristic feature which results in hypertrophy and fibrillation of airway-epithelium. According to the above guide line, the sole steroid inhalants effective to the chronic air way inflammation are now positioned as the first chosen medicine to asthma of more than middle degree.

As a result, steroids have been often used for serious asthma and atopic dermatitis as being considered as the sole effective drugs. However, it becomes problem that by using such steroids for long terms various side effects (steroid dermatitis, induced infected disease, discorticism, etc.) occur.

From the point of these views too, it has been desired to develop the drug which selectively suppresses immune responses on Th2 and inhibits both early phase and late phase reactions, or inhibits allergic inflammatory reaction characterized with infiltration and activation of eosinophils in the stage of fundamental source and is therapeutically and prophylactically effective for general allergic diseases.

Furthermore, when it is planned to develop the therapeutic or prophylactic drugs which have less side effects, it seems that the drugs which suppress immune responses on Th2 as mentioned above and enhance immune responses on Th1 simultaneously, are more preferable as medicines. As mentioned above, since Th1 play an important role for the living body, namely infection-protection against virus and bacteria by mainly producing IFN-γ, the drugs which suppress the immune responses on Th2 and enhance activity of Th1 are very preferable in view of side-effects. For example, immunosuppressives, e.g. cyclosporin or FK506 are known to strongly inhibit activation of Th2. However, both cyclosporin and FK506 show non-specific suppression against immune responses, namely not only inhibit activation of Th2, but also more strongly inhibit activation of Th1. Therefore, serious side effects such as opportunistic infection or increase of carcinogenic rate caused by such non-specific suppression against immune responses have been problem. Other non-specific immunosuppressives are also considered to have same problems.

As mentioned above, the drug which enhances immune responses on Th1 represented by production of IFNγ and suppresses immune responses on Th2 represented by production of IL-4 and IL-5 simultaneously, will be a therapeutic and prophylactic agent for allergic diseases with less side effects.

Autoimmune diseases in the state that production of an antibody or humoral immunity are abnormally enhanced, such as systemic lupus erythematosus are also considered to be in the state that immune responses of Th2 are abnormally enhanced (Medical Immunology 15, 401 (1988)). Therefore, the drug which enhances immune responses of Th1 and suppresses immune responses of Th2 is expected to become a therapeutic agent for autoimmune diseases.

Pyrimidine derivatives having general anti-virus activity are disclosed in Japanese Patent Publication A 9-301958 and Japanese Patent Publication A8-134044. However, there is no suggestion of pyrimidine derivatives of the present invention which enhances immune responses of Th1 and suppress immune responses of Th2.

SUMMARY OF INVENTION

Under such circumstances the present inventors synthesized various compounds and examined them on the effect to Th1 and Th2 immune responses. As a result, it was found that certain pyrimidine derivatives enhance Th1 immune responses and suppress Th2 immune responses and therefore, change the balance of Th1/Th2 into preferable direction.

That is, the present invention relates to:

[1] a pyrimidine derivative of the formula (1) or a salt thereof;

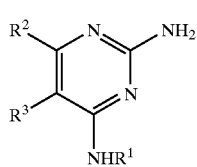

(1)

wherein $R^1$ is a formula (2);

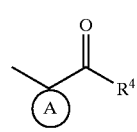

(2)

{in the formula (2),
ring A is substituted or unsubstituted $C_{3-10}$ cycloalkane, substituted or unsubstituted $C_{5-10}$ cycloalkene, substituted or unsubstituted $C_{7-10}$ bicycloalkane, or substituted or unsubstituted heterocyclic ring containing O atom or S atom as a heteroatom, and said S atom may form sulfinyl or sulfonyl together with one or two oxygen atoms, and $R^4$ is straight or branched $C_{1-10}$ alkyl, $C_{2-6}$ alkenyl, $C_{3-6}$ alkinyl, $C_{3-6}$ cycloalkyl, $C_{4-10}$ cycloalkyl-alkyl, or $OR^8$ ($R^8$ is straight or branched $C_{1-10}$ alkyl, $C_{3-6}$ alkenyl, $C_{3-6}$ alkinyl, $C_{3-6}$ cycloalkyl or $C_{4-10}$ cycloalkyl-alkyl)}, or a formula (3);

(3)

{in the formula (3),
$R^5$ is straight or branched $C_{1-10}$ alkyl; $C_{2-6}$ alkenyl; $C_{3-6}$ alkinyl; straight or branched $C_{1-10}$ alkyl substituted by hydroxy, halogen atom or $C_{1-4}$ alkoxy; phenyl; $C_{3-8}$ cycloalkyl; a 5 to 7 membered saturated heterocyclic ring containing one or two oxygen atoms as heteroatoms; or $C(=O)R^9$ ($R^9$ is straight or branched $C_{1-10}$ alkyl, $C_{2-6}$ alkenyl, $C_{3-6}$ alkinyl, $C_{3-6}$ cycloalkyl, $C_{4-10}$ cycloalkyl-alkyl, or $OR^{10}$ ($R^{10}$ is straight or branched $C_{1-10}$ alkyl, $C_{2-6}$ alkenyl, $C_{3-6}$ alkinyl, $C_{3-6}$ cycloalkyl or $C_{4-10}$ cycloalkyl-alkyl)), $R^6$ is hydrogen atom, straight or branched $C_{1-10}$ alkyl, $C_{6-10}$ aryl, halogen atom, $C_{6-10}$ aryl substituted by $C_{1-4}$ alkoxy or $C_{1-4}$ alkyl, carbamoyl, or hydroxymethyl, and $R^7$ is hydrogen atom, or straight or branched $C_{1-10}$ alkyl}, $R^2$ is hydrogen atom, or straight or branched $C_{1-10}$ alkyl, and $R^3$ is straight or branched $C_{1-10}$ alkyl; $C_{3-6}$ cycloalkyl; straight or branched $C_{1-10}$ alkyl substituted by $C_{1-2}$ alkylcarbamoyl, $C_{2-4}$ dialkylcarbamoyl, $C_{1-4}$ alkoxy, $C_{1-4}$ alkoxycarbonyl, $C_{3-6}$ cycloalkyl, hydroxy, $C_{1-4}$ alkylcarbonyloxy, halogen atom, amino, $C_{2-4}$ acyl-substituted amino, $C_{1-4}$ alkyl-substituted sulfonylamino or $C_{1-5}$ alkoxycarbonylamino; or a formula (4);

(4)

{in the formula (4), $R^{11}$ is phenyl, pyridyl, thienyl, or furyl and each of them may be substituted by one or more substituents. Said substituents are halogen atom, cyano, carbamoyl, $C_{1-4}$ alkoxy, or $C_{1-4}$ alkyl. n is integers of 0–4, provided that n is intergers of 1–4 when $R^{11}$ is phenyl.}, or $R^2$ and $R^3$ taken together are $C_{3-5}$ alkylene or said alkylene in which methylene is substituted by O atom,

[2] The pyrimidine derivative or its salt of [1], wherein $R^3$ is straight or branched $C_{1-10}$ alkyl; $C_{3-6}$ cycloalkyl; or straight or branched $C_{1-10}$ alkyl substituted by $C_{1-2}$ alkylcarbamoyl, $C_{2-4}$ dialkylcarbamoyl, $C_{1-4}$ alkoxy, $C_{1-4}$ alkoxycarbonyl, $C_{3-6}$ cycloalkyl, hydroxy, $C_{1-4}$ alkylcarbonyloxy, halogen atom, amino, $C_{2-4}$ acyl-substituted amino, $C_{1-4}$ alkyl-substituted sulfonylamino or $C_{1-5}$ alkoxycarbonylamino; or $R^2$ and $R^3$ taken together are $C_{3-5}$ alkylene or said alkylene in which methylene is substituted by O atom,

[3] The pyrimidine derivative or its pharmaceutically acceptable salt of [1] or [2], wherein $R^2$ and $R^3$ taken together is trimethylene or tetramethylene,

[4] The pyrimidine derivative or its pharmaceutically acceptable salt of [1] or [2], wherein $R^3$ is straight or branched $C_{1-7}$ alkyl,

[5] The pyrimidine derivative or its pharmaceutically acceptable salt of [1], wherein R³ is the formula (4);

wherein R¹¹ and n are the same defined above,

[6] The pyrimidine derivative or its pharmaceutically acceptable salt of [1] or [5], wherein R¹¹ of the formula (4) is pyridyl, thienyl or furyl,

[7] The pyrimidine derivative or its pharmaceutically acceptable salt of [1], [5] or [6], wherein n of the formula (4) is integers 2–4,

[8] The pyrimidine derivative or its pharmaceutically acceptable salt of any one of [1] to [7], wherein R¹ is the formula (2);

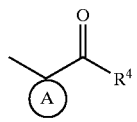

wherein the ring A and R⁴ are the same defined above,

[9] The pyrimidine derivative or its pharmaceutically acceptable salt of any one of [1] to [7], wherein R¹ is the formula (3);

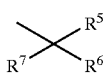

wherein ring R⁵, R⁶ and R⁷ are the same defined above,

[10] The pyrimidine derivative or its pharmaceutically acceptable salt of any one of [1] to [7] or [9], wherein R⁵ is straight $C_{2-4}$ alkyl or straight $C_{2-4}$ alkyl substituted by hydroxy,

[11]. An immunomodulator which suppresses immune responses of type 2 helper T cell and enhances immune responses of type 1 helper T cell, comprising the pyrimidine derivative or its pharmaceutically acceptable salt of any one of [1] to [10] as an active ingredient,

[12] A therapeutic or prophylactic agent for diseases in the state that immune responses of type 2 helper T cell are abnormally enhanced, comprising the pyrimidine derivative or its pharmaceutically acceptable salt of any one of [1] to [10] as an active ingredient,

[13] The therapeutic or prophylactic agent of [12], wherein the disease in the state that immune responses of type 2 helper T cell are abnormally enhanced is an allergic disease, and

[14] The therapeutic or prophylactic agent of [13], wherein the allergic disease is asthma, allergic rinitis, or allergic dermatitis.

DETAILED EXPLANATION OF INVENTION

The present invention is explained in detail below.

Definition of Words

"Substituents R¹, R² and R³" on pyrimidine ring of the present invention are explained as follows:

In regard to R¹, examples of $C_{3-10}$ cycloalkane in ring A are cyclopropane, cyclobutane, cyclopentane, cyclohexane, cycloheptane, cyclooctane, etc. Examples of $C_{5-10}$ cycloalkene are cyclopentene, cyclohexene, etc. Examples of $C_{7-10}$ bicycloalkane are bicyclo[2.2.1]heptane, bicyclo[2.2.1]hepta-5-ene, bicyclo[2.2.2]octane, bicyclo[2.2.2]octa-5-ene, etc. Examples of hererocyclic ring containing O atom or S atom as a heteroatom are oxetane, thietane (trimethylenesulfide), thietane-1-oxide (trimethylenesulfoxide), thietane-1,1-dioxide (trimethylenesulfone), tetrahydrofuran, tetrahydrothiophene, tetrahydrothiophene-1-oxide, tetrahydrothiophene-1,1-dioxide, tetrahydro-4H-pyran, thian (pentamethylenesulfide), thian-1,1-dioxide (pentamethylenesulfone), thian-1-oxide (pentamethylenesulfoxide), oxepane (hexamethyleneoxide), thiepane (hexamethylenesulfide), thiepane-1-oxide (hexamethylenesulfoxide), thiepane-1,1-dioxide (hexamethylenesulfone), 7-oxabicyclo[2.2.1]heptane, 7-oxabicyclo[2.2.1]hepta-5-ene, etc., and examples of substituents of substituted cycloalkane, substituted cycloalkene, substituted bicycloalkane and substituted heterocyclic ring in ring A are $C_{1-3}$ alkyl, hydroxy, $C_{1-3}$ alkoxycarbonyl, carboxy, carbamoyl, etc. And said substituents on the adjacent carbon atoms may form tetramethylene bridge, or carbon atom(s) in the ring may be substituted by carbonyl(C=O). Said substituent(s) are one or more and the same or different. Examples of $C_{1-3}$ alkyl are methyl, ethyl, n-propyl, 2-propyl, etc. Examples of $C_{1-3}$ alkoxycarbonyl are methoxycarbonyl, ethoxycarbonyl, n-propoxycarbonyl, 2-propoxycarbonyl, etc.

Examples of straight or branched $C_{1-10}$ alkyl in R², R³, R⁴, R⁵, R⁶, R⁷, R8, R⁹ and R¹⁰ are methyl, ethyl, propyl, 1-methylethyl, butyl, 1-methylpropyl, 2-methylpropyl, pentyl, 1-methylbutyl, 2-methylbutyl, 3-methylbutyl, 1-ethylpropyl, hexyl, 1-methylpentyl, 2-methylpentyl, 3-methylpentyl, 4-methylpentyl, 1-ethylbutyl, 2-ethylbutyl, heptyl, octyl, nonyl, decyl, etc.

Examples of $C_{2-6}$ alkenyl in R⁴, R⁵, R⁸, R⁹ and R¹⁰ are vinyl, allyl, butenyl, pentenyl, hexenyl, etc.

Examples of $C_{2-6}$ alkenyl in R⁴, R⁵, R⁸, R⁹ and R¹⁰ are propargyl, butinyl, pentinyl, etc.

Examples of $C_{3-8}$ cycloalkyl in substituents of straight or branched $C_1$lo alkyl in R³, R⁴, R⁵, R⁸, R⁹ and R¹⁰ are cyclopropyl, cyclobutyl, cyclopentyl, cyclohexyl, cycloheptyl, cyclooctyl, etc.

Examples of $C_{4-10}$ cycloalkyl-alkyl in R⁴, R⁸, R⁹ and R¹⁰ are cyclopropylmethyl, cyclobutylmethyl, cyclopentylethyl, cyclohexylmethyl, cyclohexylpropyl, etc.

Examples of halogen atoms in R³, R⁵ and R⁶ are fluorine atom, chlorine atom, bromine atom, or iodine atom.

Examples of $C_{1-4}$ alkoxy in R³, R⁵ and R⁶ are methoxy, ethoxy, propoxy, butoxy, etc.

Preferable examples of straight or branched $C_{1-10}$ alkyl in R³ is straight or branched $C_{1-7}$ alkyl, e.g. methyl, ethyl, propyl, 1-methylethyl, butyl, 1-methylpropyl, 2-methylpropyl, pentyl, 1-methylbutyl, 2-methylbutyl, 3-methylbutyl, 1-ethylpropyl, hexyl, heptyl, etc.

In regard to substituents of straight or branched $C_{1-10}$ alkyl in R³, examples of $C_{1-2}$ alkylcarbamoyl is methylcarbamoyl, ethylcarbamoyl, etc.; examples of $C_{2-4}$ dialkylcarbamoyl is dimethylcarbamoyl, methylethylcarbamoyl, diethylcarbamoyl, etc.; examples of $C_{1-4}$ alkoxycarbonyl are methoxycarbonyl, ethoxycarbonyl, propoxycarbonyl, 2-propoxycarbonyl, etc.; examples of $C_{1-4}$ alkylcarbonyloxy are acetoxy, ethylcarbonyloxy, propylcarbonyloxy, etc., examples of amino substituted by $C_{2-4}$ acyl are acetylamino, propanoylamino, etc.; examples of sulfonylamino substituted by $C_{1-4}$ alkyl are methylsulfonylamino, ethylsulfonylamino, propylsulfonylamino, butylsulfonylamino, etc.; examples of $C_{1-5}$ alkoxycarbonylamino are methoxycarbonylamino, ethoxycarbonylamino, propyloxycarbonylamino, butoxycarbonylamino, etc.

$R^{11}$ in $R^3$ means phenyl, pyridyl, thienyl, or furyl, and each of them may be substituted by one or more substituents. Phenyl and pyridyl are preferable, and phenyl is especially preferable. The substituents are halogen atoms, such as F, Cl, Br, etc., cyano, carbamoyl, $C_{1-4}$ alkoxy, such as methoxy, ethoxy, propoxy, etc., $C_{1-4}$ alkyl, such as methyl, ethyl, propyl, butyl, etc. n is integers 0–4, provided that n is integers 1–4 when $R^{11}$ is phenyl. n is preferably integers 0–2, more preferably 1 or 2.

Examples of a 5 to 7 membered saturated heterocyclic ring containing one or two oxygen atoms as heteroatoms in $R^5$ are tetrahydrofuran, oxane, 1,4-dioxane, oxepane, etc.

Preferable substituents of straight or branched $C_{1-10}$ alkyl in $R^5$ are hydroxy, its preferable number are one or more, and its preferable position is 1 or 2 (position 2 or 3 on counting from amino group of pyrimidine ring). When the substituent of straight or branched $C_{1-10}$ alkyl in $R^5$ is hydroxy, its position is preferably not the end position of the alkyl chain.

Examples of $C_{6-10}$ aryl in $R^6$ are phenyl, naphthyl, etc.

Preferable examples of straight or branched $C_{1-10}$ alkyl in $R^9$ is straight or branched $C_{2-4}$ alkyl, e.g. ethyl, propyl, 1-methylethyl, butyl, etc.

Examples of $C_{3-6}$ alkylene which $R_2$ and $R_3$ taken together form are trimethylene, tetramethylene, pentamethylene, etc. They are illustrated as following formulas (4), (5) and (6);

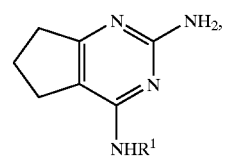
(4)

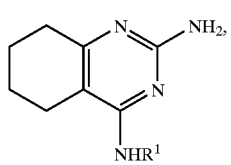
(5)

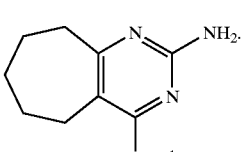
(6)

Examples of $C_{3-5}$ alkylene which $R_2$ and $R_3$ taken together form in which methylene is substituted by O atom, are oxybismethylene, oxymethyleneethylene, oxybisethylene, etc. They are illustrated as following formulas (7), (8), (9), (10), (11) and (12);

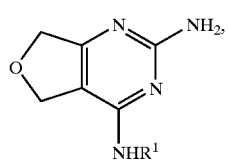
(7)

(8)

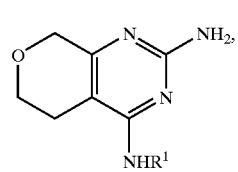
(9)

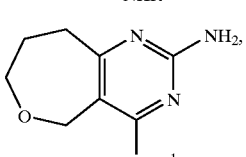
(10)

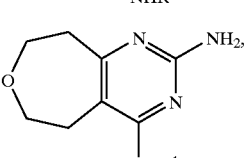
(11)

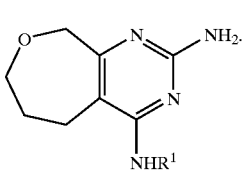
(12)

The pyrimidine derivatives of the present invention being active ingredients as medical drugs are formed into pharmaceutically acceptable salts. As pharmaceutically acceptable salts, there are illustrated acid addition salts and base addition salts. As acid addition salts, there are illustrated inorganic acid salts, such as hydrochloride, hydrobromide, sulfate or phosphate, or organic acid salts, such as citrate, oxalate, malate, tartrate, fumarate or maleate. As base addition salts, there are inorganic base salts such as sodium salts or calcium salts, or organic base salts, such as meglumine salt, tris(hydroxymethyl)aminomethane salt. The pyrimidine derivatives of the present invention or pharmaceutically acceptable salts thereof also include solvates such as hydrates, etc.

The compounds of the formula (1) of the present invention can be prepared by the following method or according to the following method.

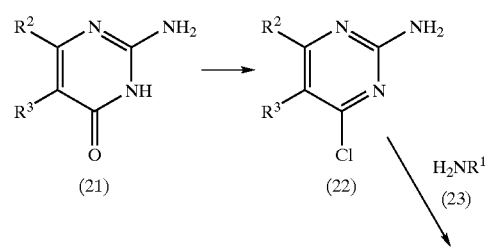

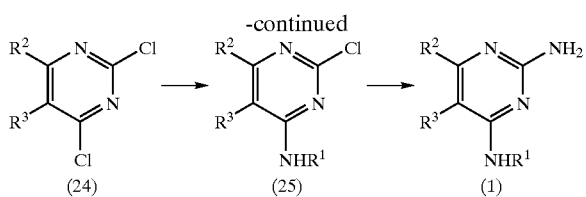

wherein $R^1$, $R^2$ and $R^3$ are the same as defined in the formula (1) above.

PROCESS 1

The compound (22) is prepared by reacting the compound (21) with phosphorus oxychloride. The reaction may be carried out, if necessary in the presence of a solvent. As the solvents, there are aromatic hydrocarbons such as toluene or xylene. The reaction may be carried out in the presence of a reaction promoter such as N,N-dimethylaminopyridine. The reaction temperature is selected between room temperature and reflux temperature of the solvent.

The compound (1) of the present invention can be prepared by reacting the compound (22) with the compound (23). As the solvents, there are aromatic hydrocarbons such as toluene or xylene, ethers such as tetrahydrofuran (THF) or dioxane, alcohols, such as ethanol, 2-propanol or butanol, or inert solvents such as dimethylformamide (DMF) or acetonitrile. The reaction is carried out, if necessary in the presence of an organic base such as triethylamine, or an inorganic base such as sodium carbonate or potassium carbonate. The reaction temperature is selected between for example, room temperature and reflux temperature of the solvent.

PROCESS 2

The compound (25) can be prepared by reacting the compound (24) with the compound (23). As the solvents, there are aromatic hydrocarbons such as toluene or xylene, ethers such as tetrahydrofuran (THF) or dioxane, alcohols such as ethanol, 2-propanol or butanol, or inert solvents such as dimethylformamide (DMF) or acetonitrile. The reaction may be carried out, if necessary in the presence of an organic base such as triethylamine, or an inorganic base such as sodium carbonate or potassium carbonate. The reaction temperature is selected between for example, room temperature and reflux temperature of the solvent.

The compound (1) of the present invention can be prepared by reacting the compound (25) with ammonia in a solvent. As the solvents, there are alcohols such as methanol or ethanol ethers such as dioxane or ethyleneglycol dimethyl ether. The reaction is carried out in an autoclave at room temperature to about 200° C.

The compound (1) of the present invention can also be prepared by reacting the compound (25) with sodium azide, followed by reduction with triphenyl phosphine. The reaction with sodium azide is carried out in an inert solvent such as DMF, etc. The reaction temperature is selected from about room temperature to around the boiling point of the solvent. Reduction by triphenyl phosphine is carried out in an ether such as THF, etc. The reaction temperature is selected from about room temperature to around the boiling point of the solvent.

The compounds of the formula (1) of the present invention and intermediates for preparing them can be purified with conventional methods such as column chromatography, recrysatallization, etc. As the solvents for recrystallization there are alcohols such as methanol, ethanol or 2-propanol, ethers such as diethyl ether, esters such as ethyl acetate, aromatic hydrocarbons such as toluene, ketones such as acetone, hydrocarbons such as hexane, or a mixture thereof.

In case of carrying out above reactions, protection or deprotection techniques are, if necessary, employed. The protection or deprotection techniques are in detail described in "Protecting Groups in Organic Synthesis" by T. W. Greene and P. G. M. Wuts (1991), JOHN WILEY & SONS INC.

The pyrimidine derivatives of the present invention or pharmaceutically acceptable salts thereof can form solvates such as hydrates and therefore, the present invention also includes the solvates.

When the compounds of the present invention have an asymmetric carbon atom(s), optical isomers exist and therefore, a mixture thereof and an isolated optical isomer are included in the compounds of the present invention. In order to purify such an optical isomer, optical resolution is employed.

As to to optical resolution, the compounds of the present invention or intermediates thereof can be formed salts with an optically active acid (e.g. monocarboxylic acid such as mandelic acid, N-benzyloxyalanine or lactic acid, dicarboxylic acid such as tartaric acid, O-diisopropylidene tartaric acid or malic acid, or sulfonic acids such as camphersulfonic acid, bromocampher-sulfonic acid) in an inert solvent (e.g. alcohols such as methanol, ethanol or 2-propanol, ethers such as diethyl ether, esters such as ethyl acetate, aromatic hydrocarbons such as toluene, acetonitrile or a mixture thereof).

When the compounds of the present invention or intermediates thereof have an acidic substituent such as carboxy group, etc., they can be formed salts with an optically active amine (e.g. an organic amine such as α-phenethylamine, quinine, quinidine, cinchonidine, cinchonine, strychnine, etc.), too.

The temperature forming salts is from room temperature to the boiling point of the solvent. In order to increase the optical purity of the compound, the temperature is preferably raised once to around the boiling point of the solvent. The yield can be increased, if necessary by cooling the solvent before filtering a precipitated salt. The amount of an optically active acid or amine is about 0.5–2.0 equimoles to the substrate, preferably about 1 equimole. If necessary, the crystals are recrystallized in an inert solvent (e.g. alcohols such as methanol, ethanol or 2-propanol, ethers such as diethyl ether, esters such as ethyl acetate, aromatic hydrocarbons such as toluene, acetonitrile or a mixture thereof) to be obtainable an optically active salt with highly optical purity. The obtained salt, if necessary is treated in the conventional manner with an acid or a base to obtain a free compound.

The pyrimidine derivatives of the present invention can be orally or parenterally administered. In case of oral administration, the compound is administered in the conventional administration form. In case of parenteral administration, the compound can be administered in a topical administration forms, injections, transdermal application forms or nasal application forms. Preparations for oral or rectal administration include for example, capsules, tablets, pills, powders, cashes, suppositories, solutions, etc. Injections include for example, sterilized solutions or emulsions, etc. Topical administration preparations include, for example creams, ointments, lotions, transdermal preparations (usual paches, matrixs), etc.

The above preparations are prepared with pharmaceutically acceptable fillers and additives by the conventional method. Pharmaceutically acceptable fillers and additives include carriers, binders, flavors, buffering agents, viscosity-increasing agents, coloring agents, stabilizing agents, emulsifiers, dispersing agents, suspending agents, preservatives, etc.

Pharmaceutically acceptable carriers include, for example magnesium carbonate, magnesium stearate, talc, sugar, lactose, pectin, dextrin, starch, gelatin, tragacanth, methylcellulose, sodium carboxymethyl cellulose, wax (lower melting point), cacao butter, etc. Capsules can be prepared by putting the compound of the present invention with pharmaceutically acceptable carriers. The compound of the present invention is mixed with pharmaceutically acceptable fillers and the mixture is put into capsules, or the compound without any filler is put into capsules. Caches can be prepared by the same method as the capsules.

Solutions for injection include, for example solutions, suspensions, emulsions, etc. such as an aqueous solution, water-propylene glycol solution. The solution may contain water and can be prepared in propylene glycol or/and propylene glycol solution. The solutions suitable for oral administration can be prepared by adding the compound of the present invention into water and if necessary, adding a coloring agent, a flavor, a stabilizing agent, a sweetening, a solubilizing agent, a viscosity-increasing agent, etc. Also the solutions suitable for oral administration can be prepared can be prepared by adding the compound of the present invention and a dispersing agent into water to make viscositic solutions. The viscosity-increasing agents include, for example natural or synthetic gum, resin, methylcellulose, sodium carboxymethyl cellulose, or known emulsifiers.

The preparations for topical administration include for example above mentioned solutions, creams, aerosols, sprays, powders, lotions, ointments, etc. The preparations for topical administration can be prepared by mixing the compound of the present invention, pharmaceutically acceptable diluents and carriers conventionally used. Creams and ointments can be prepared, for example by mixing aqueous or oil bases and viscosity-increasing agents and/or gelating agents. The bases include, for example water, liquid paraffin, plant oil (peanut oil, castor oil), etc. The viscosity-increasing agents include, for example soft paraffin, aluminum stearate, cetostearyl alcohol, propylene glycol, polyethylene glycol, lanolin, hydrogenated lanolin, bees wax, etc. The lotions can be prepared by mixing aqueous or oil bases, and one or more pharmaceutically acceptable stabilizing agents, suspending agents, emulsifiers, dispersing agents, viscosity-increasing agents, coloring agents, flavors, etc.

The powders are prepared with pharmaceutically acceptable powder bases. The bases are talc, lactose, starch, etc. Drops can be prepared with aqueous or non-aqueous bases and one or more pharmaceutically acceptable dispersing agents, suspending agents, solbilizing agents, etc.

The preparations for topical administration may contain, if necessary preservatives, such as hydroxy benzoic acid methyl ester, hydroxy benzoic acid propyl ester, chloro cresol, benzalkonium chloride, and antibacterial agents.

Liquids for spray, powders or drops containing the compound of the present invention can be nasally administered.

Dose and number of administration vary with a disease to be treated, age, body weight, route of administration. In case of oral administration, an active ingredient is administered to an adult generally about 1–500 mg per day, preferably about 5–100 mg, once or several times. In case of injections, an active ingredient is administered generally about 0.1–300 mg per day, preferably about 1–100 mg, once or several times.

EXAMPLE

The present invention is in more detail explained by examples, reference-examples and tests, but the present invention should not be limited to them.

Example 1

Ethyl-2-[(2-Amino-5,6,7,8-tetrahydroquinazoline-4-yl)amino]acetate

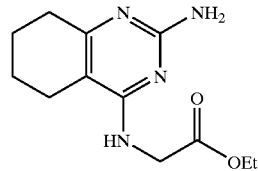

To a mixture of 4-chloro-5,6,7,8-tetrahydroquinazoline-2-ylamine (100 mg, 0.545 mmol), triethylamine (221 mg, 2.18 mmol) and butanol (3 ml) was added glycine ethyl ester hydrochloride (152 mg, 100 mmol) at room temperature. After the mixture was stirred for 4 hours at 90° C., the reaction mixture was poured into water and extracted with chloroform. The organic layer was washed with saturated brine, dried over sodium sulfate, filtered and the solvent in the filtrate was removed in vacuo. The residue was purified by silica gel chromatography (3% MeOH/CHCl$_3$) to give the object compound (98.3 mg, 72.1%).

$^1$H-NMR (CDCl$_3$): δ 1.30 (3H, t, J=7.0 OHz), 1.78 (4H, m), 2.30 (2H, m), 2.55 (2H, m), 4.20 (2H, m), 4.24 (2H, q, J=7.0 Hz), 4.76 (2H, bs), 5.13 (1H, bs).

Example 2

N-(2-Amino-5,6,7,8-tetrahydroquinazoline-4-yl)-N-(cyclohexylmethyl)amine

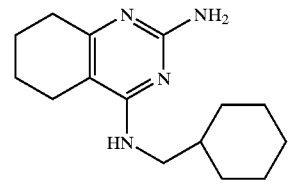

A mixture of 4-chloro-5,6,7,8-tetrahydroquinazoline-2-ylamine (107 mg, 0.58 mmol), triethylamine (221 mg, 2.18 mmol), cyclohexylmethylamine (132 mg, 1.17 mmol) and n-butanol (3 ml) was reacted for 4 hours at 80–90° C. According to the post-treatment of Example 1, the object compound was obtained (102 mg, 67.9%).

$^1$H-NMR (CDCl$_3$): δ 0.97 (2H, m), 1.22 (3H, m), 1.56 (1H, m), 1.76 (9H, m), 2.21 (2H, m), 2.55 (2H, m), 3.28 (2H, t, J=6.8 Hz), 4.71 (1H, bt), 5.03 (2H, bs).

Example 3

Ethyl-2-[(2-Amino-5,6,7,8-tetrahydroquinazoline-4-yl)amino]-4-methylpentanoate

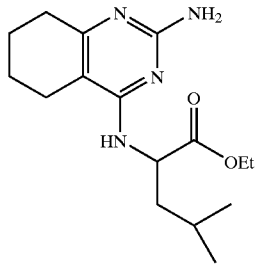

A mixture of 4-chloro-5,6,7,8-tetrahydroquinazoline-2-ylamine (117 mg, 0.64 mmol), triethylamine (259 mg, 2.56 mmol), dl-leucine ethyl ester hydrochloride (250 mg, 1.28 mmol) and n-butanol (2 ml) was reacted for 6 hours at 80–90° C. According to the post-treatment of Example 1, the object compound was obtained (104.3 mg, 72.1%).

$^1$H-NMR (CDCl$_3$): δ 0.92 (6H, m), 1.30 (3H, t, J=7.1 Hz), 1.60–1.70 (3H, m), 1.79 (4H, m), 2.29 (2H, m), 2.54 (2H, m), 4.18 (2H, q, J=7.1 Hz), 4.80 (1H, m), 4.88 (2H, bs), 4.90 (1H, bs).

Example 4

N-(2-Amino-5,6,7,8-tetrahydroquinazoline-4-yl)-N-(2-ethoxyethyl)amine

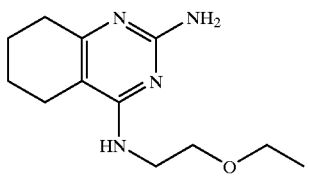

To a mixture of 4-chloro-5,6,7,8-tetrahydroquinazoline-2-ylamine (100 mg, 0.545 mmol), triethylamine (221 mg, 2.18 mmol) and dimethylformamide (2 ml) was added ethoxyethylamine (98 mg, 1.10 mmol) at room temperature. After the mixture was stirred for 2.5 hours at 90° C., the reaction mixture was poured into water and extracted with chloroform. The organic layer was washed with saturated brine, dried over sodium sulfate, filtered and the solvent in the filtrate was removed in vacuo. The residue was purified by preparative TLC (10% MeOH/CHCl$_3$) to give the object compound (41.7 mg, 32.4%).

$^1$H-NMR (CDCl$_3$): δ 1.22 (3H, t, J=6.8 Hz), 1.80 (4H, m), 2.23 (2H, m), 2.59 (2H, m), 3.53 (2H, q, J=6.8 Hz), 3.62 (4H, m), 5.17 (1H, bt), 5.30 (2H, bs).

Example 5

N-(2-Amino-5,6,7,8-tetrahydroquinazoline-4-yl)-N-butylamine

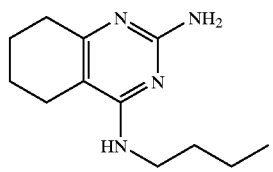

A mixture of 4-chloro-5,6,7,8-tetrahydroquinazoline-2-ylamine (100 mg, 0.545 mmol) and butylamine (2 ml) was stirred for 4 hours at 90° C. The reaction mixture was poured into water and extracted with chloroform. The organic layer was washed with saturated brine, dried over sodium sulfate, filtered and the solvent in the filtrate was removed in vacuo. The residue was purified by column chromatography (10% MeOH/CHCl$_3$) to give the object compound (94.5 mg, 78.9%).

$^1$H-NMR (CDCl$_3$): δ 5 0.93 (3H, t, J=7.0 Hz), 1.36 (2H, m), 1.63 (2H, m), 1.78 (4H, m), 2.31 (2H, m), 2.58 (2H, m), 3.47 (2H, q, J=7.0 Hz), 6.00 (1H, bs), 6.03 (1H, t like), 7.34 (1H, bs).

Example 6

N-(2-Amino-5,6,7,8-tetrahydroquinazoline-4-yl)-N-hexylamine

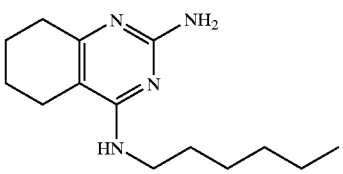

According to the method of Example 5, the above compound was obtained.

$^1$H-NMR (CDCl$_3$): δ 0.89 (3H, m), 1.32 (6H, m), 1.59 (2H, m), 1.81 (4H, m), 2.21 (2H, m), 2.62 (2H, m), 3.44 (2H, q, J=7.0 Hz), 4.99 (1H, bs), 5.73 (2H, brs).

Example 7

Ethyl 2-[(2-Amino-5,6,7,8-tetrahydroquinazoline-4-yl)amino]propanoate

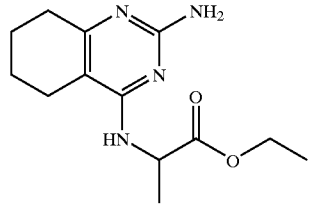

To a mixture of 4-chloro-5,6,7,8-tetrahydroquinazoline-2-ylamine (100 mg, 0.545 mmol), triethylamine (221 mg, 2.18 mmol) and dimethylformamide (4 ml) was added 2-aminopropionic acid ethyl ester hydrochloride (167 mg, 1.09 mmol) at room temperature. After the mixture was stirred for 2.5 hours at 100° C., the reaction mixture was poured into water and extracted with chloroform. The organic layer was washed with saturated brine, dried over sodium sulfate, filtered and the solvent in the filtrate was removed in vacuo. The residue was purified by silica gel chromatography (5% MeOH/CHCl₃) to give the object compound (42.1 mg, 29.3%).

¹H-NMR (300 MHz, CDCl₃): δ 5.07 (brd, 1H, J=6.8 Hz), 4.79–4.69 (3H, m), 4.21 (q, 2H, J=7.1 Hz), 2.56–2.53 (2H, m), 2.32–2.25 (2H, m), 1.85–1.73 (4H, m), 1.47 (d, 3H, J=7.1 Hz), 1.29 (t, 3H, J=7.1 Hz).

Example 8

Ethyl 2-[(2-Amino-5,6,7,8-tetrahydroquinazoline-4-yl)amino]-3-hydroxypropanoate

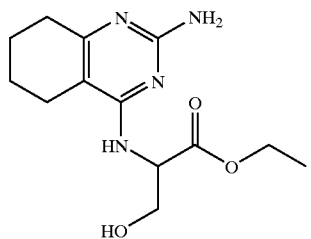

According to the method of Example 7, the above compound was obtained.

1H-NMR (300 MHz, CDCl₃): δ 5 5.63 (d, 1H, J=6.2 Hz), 4.84–4.76 (3H, m), 4.26–4.20 (2H, m), 4.08 (dd, 1H, J=11.0, 3.1 Hz), 3.94 (dd, 1H, J=11.0, 1.9 Hz), 2.55–2.47 (2H, m), 2.32–2.25 (2H, m), 1.80–1.70 (4H, m), 1.31 (t, 3H, J=7.1 Hz).

Example 9

Methyl 2-[(2-Amino-5,6,7,8-tetrahydroquinazoline-4-yl)amino]hexanoate

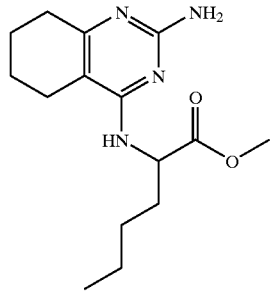

According to the method of Example 7, the above compound was obtained.

¹H-NMR (300 MHz, CDCl₃): δ 4.94 (d, 1H, J=7.7 Hz), 4.85–4.75 (1H, m), 4.74 (1H, brs), 3.74 (3H, s), 2.57–2.50 (2H, m), 2.30–2.50 (2H, m), 1.95–1.65 (6H, m), 1.40–1.25 (4H, m), 0.92–0.87 (3H, m).

Example 10

2-[(2-Amino-5,6,7,8-tetrahydroquinazoline-4-yl)amino]hexane-1-ol

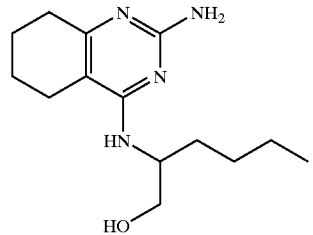

Methyl 2-[(2-amino-5,6,7,8-tetrahydroquinazoline-2-ylamino]hexanoate (122 mg, 0.417 mmol) was dissolved in THF (3 ml). To the solution was added lithium aluminum hydride (15 mg, 0.417 mmol) at 0° C. and it was warmed to room temperature. The reaction mixture was cooled and THF (10 ml) was dropped thereto, followed by dropping water (1 ml). Then 1M NaOH aqueous solution was added until the solid developed. MgSO₄ was added to the reaction mixture and the mixture was filtered. To the filtrate were added a saturated aqueous sodium hydrogen carbonate solution and chloroform and it was extracted. The organic layer was washed with saturated brine, dried over sodium sulfate, filtered and the solvent in the filtrate was removed in vacuo. The residue was purified by preparative TLC (15% MeOH/CHCl₃) to give the object compound (27 mg, 24.5%).

¹H-NMR (300 MHz, CDCl₃): δ 5.46 (brs, 1H), 4.97 (d, 1H, J=7.1 Hz), 4.50 (2H, brs), 4.20–4.10 (1H, m), 3.76 (dd, 1H, J=11.0, 3.1 Hz), 3.62 (dd, 1H, J=11.0, 6.6 Hz), 2.60–2.50 (2H, m), 2.35–2.15 (2H, m), 1.85–1.70 (4H, m), 1.70–1.45 (2H, m), 1.40–1.35 (4H, m), 0.93–0.88 (3H, m).

Example 11

1-[(2-Amino-5,6,7,8-tetrahydroquinazoline-4-yl)amino]pentane-2-ol

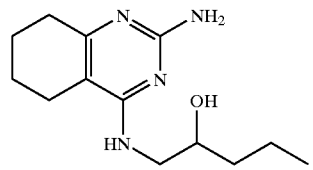

A mixture of 4-chloro-5,6,7,8-tetrahydroquinazoline-2-ylamine (184 mg, 1 mmol), 2-hydroxypentylamine hydrochloride (140 mg, 1 mmol), triethylamine (202 mg, 2 mmol) and DMF (1 ml) was warmed for 5 hours in a bath (bath temperature, 90° C.). The solvent in the filtrate was removed in vacuo and the residue was purified by silica gel column chromatography (CHCl₃:MeOH:NH₄OHaq=100:10:0.4) to give the crude product (210 mg). To the crude product was aqueous ammonia solution (5 ml) and chloroform (30 ml) and it was extracted. The organic layer was washed with saturated brine (20 ml), dried over sodium sulfate, filtered and the solvent in the filtrate was removed in vacuo to give the object compound (128 mg, 51%).

¹H-NMR (300 MHz, CDCl₃): δ 4.93 (1H, brm), 4.62 (2H, brs), 3.75–3.85 (1H, m), 3.55–3.65 (1H, m), 3.33–3.44 (1H, m), 2.50–2.54 (2H, m), 2.20–2.22 (2H, m), 1.77–1.79 (4H, m), 1.38–1.54 (4H, m), 0.95 (3H, t, J=7.3 Hz).

Example 12

1-[(2-Amino-5,6,7,8-tetrahydroquinazoline-4-yl)amino]pentane-2-one

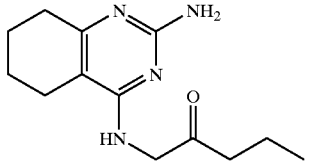

To a solution of 1-[2-amino-5,6,7,8-tetrahydroquinazoline-4-yl)amino]pentane-2-ol (120 mg, 0.479 mmol) in dichloromethane (20 ml) was added pyridinium chlorochromate (517 mg, 23.97 mmol) and the mixture was stirred for 3.5 hours. Silica gel (10 g) was added to the reaction mixture and it was filtered. The silica gel was washed with 5% MeOH/CHCl₃. The filtrates were collected and the solvent was removed in vacuo. The residue was purified by silica gel chromatography (CHCl₃:MeOH:NH₄OHaq=100:5:0.4) to give the object compound (32 mg, 26%).

$^1$H-NMR (300 MHz, CDCl₃): δ 5.36 (1H, brs), 4.62 (2H, brs), 4.28 (2H, d, J=4.0 Hz), 2.46–2.57 (4H, m), 2.30–2.32 (2H, m), 2.02 (1H, brm), 1.65–1.81 (6H, m), 0.96 (3H, t, J=7.3 Hz).

Example 13

N-(2-Amino-5,6,7,8-tetrahydroquinazoline-4-yl)-N-(tetrahydorofuran-2-yl methyl) amine

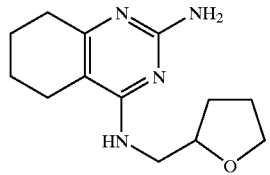

A mixture of 4-chloro-5,6,7,8-tetrahydroquinazoline-2-ylamine (184 mg, 1 mmol), tetrahydrofurfurylamine (101 mg, 1 mmol) and diethyleneglycol diethyl ether (1 ml) was kept to warm for 2 hours at 100–110° C. The reaction mixture was extracted with ethyl acetate (50 ml) and a saturated aqueous sodium hydrogen carbonate (20 ml). The organic layer was washed with saturated brine, dried over sodium sulfate, filtered and the solvent in the filtrate was removed in vacuo. The residue was purified by column chromatography (CHCl₃:MeOH:NH₄OHaq=100:10:0.4) to give the object compound (80 mg, 32.3%).

$^1$H-NMR (300 MHz, CDCl₃): δ 5 4.98 (1H, brs), 4.87 (1H, brs), 4.01–4.11 (1H, m), 3.71–3.92 (3H, m), 3.29–3.38 (1H, m), 3.14 (1H, brm), 2.54–2.58 (2H, m), 2.22–2.24 (2H, m), 1.77–2.07 (8H, m).

Example 14

N-(2-Amino-5-butyl-6-methylpyrimidine-4-yl)-N-pentylamine

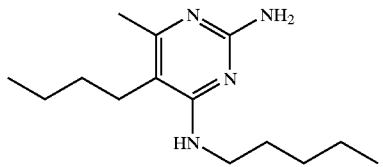

A mixture of 5-butyl-4-chloro-6-methylpyrimidine-2-yl amine (100 mg, 0.5 mmol) and amylamine (2 ml) was refluxed for 11 hours. The reaction mixture was cooled and the solvent was removed in vacuo and the residue was purified by silica gel column chromatography (MeOH:CHCl₃=1:20) to give the object compound (98 mg, 78%) as an oil.

$^1$H-NMR (CDCl₃): δ 0.93 (6H, m), 1.37 (8H, brm), 1.60 (2H, m), 2.30 (3H, s), 2.32 (2H, m), 3.44 (2H, q-like), 4.96 (1H, br), 5.59 (2H, br).

Example 15

N-(2-Amino-5-hexyl-6-methylpyrimidine-4-yl)-N-pentylamine

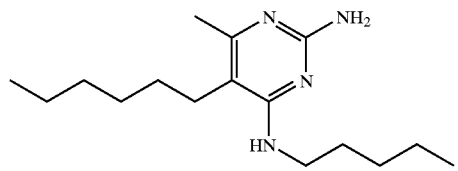

A mixture of 4-chloro-5-hexyl-6-methylpyrimidine-2-ylamine (1.00 mg, 0.44 mmol) and amylamine (2 ml) was refluxed for 11 hours. The reaction mixture was cooled and the solvent was removed in vacuo. The residue was purified by silica gel column chromatography (MeOH:CHCl₃=1:20) to give the object compound (107 mg, 87%) as an oil.

$^1$H-NMR (TMS/CDCl₃): δ 0.91 (6H, m), 1.36 (12H, brm), 1.60 (2H, m), 2.29 (3H, s), 2.31 (2H, m), 3.43 (2H, q-like), 4.90 (1H, br), 5.50 (2H, br)

Example 16

N-(2-Amino-7,8-dihydro-5H-pyrano[4,3-d]pyrimidine-4-yl)-N-pentylamine

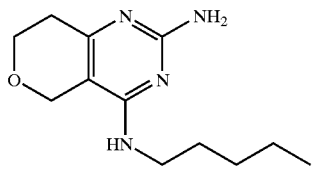

A mixture of 4-chloro-7,8-dihydro-5H-pyrano[4,3-d]pyrimidine-2-ylamine (29.3 mg, 0.158 mmol) and amylamine (1.0 ml) was refluxed for 2.5 hours. After reaction, the procedure according to pro-treatment of Example 7 was carried out to give the object compound (22.3 mg, 59%).

$^1$H-NMR (300 MHz, CDCl₃): δ 4.86 (2H, brs), 4.40 (2H, d, J=1.1 Hz), 4.09 (1H, brs), 3.94 (2H, t, J=5.6 Hz), 3.41

(2H, dt, J=7.1,5.4 Hz), 2.64 (2H, t, J=5.6 Hz), 1.64–1.50 (2H, m), 1.42–1.25 (4H, m), 0.96–0.86 (3H, m).

EXAMPLE 17

N-(2-Amino-6-butyl-5-methylpyrimidine-4-yl)-N-pentylamine

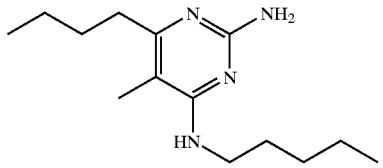

A mixture of 4-butyl-6-chloro-5-methylpyrimidine-2-ylamine (93.5 mg, 0.47 mmol) and amylamine (1.5 ml) was refluxed for 8 hours. After reaction, the procedure according to pro-treatment of Example 7 was carried out to give the object compound (50 mg, 42.7%).

$^1$H-NMR (CDCl$_3$): δ 0. 93 (6H, tx2), 1.37 (6H, m), 1.57 (4H, m), 1.91 (3H, s), 2.51 (2H, t, J=7.6 Hz), 3.40 (2H, q, J=7.3 Hz), 4.61 (1H, bs), 4.98 (2H, bs).

Example 18

N-(2-Amino-5,6-dimethylpyrimidine-4-yl)-N-pentylamine

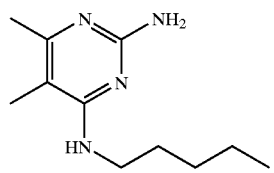

A mixture of N-(2-chloro-5,6-dimethylpyrimidine-4-yl)-N-pentylamine (131 mg, 0.575 mmol) and 5M ammonia-ethanol (40 ml) was kept at 170° C. for 10 hours. The reaction mixture was concentrated in vacuo, purified by preparative TLC (20%MeOH/CHCl$_3$) to give the object compound (4.2 mg, 3.5%).

$^1$H-NMR (300 MHz, CDCl$_3$): δ 5.17 (2H, brs), 4.56 (1H, brs), 3.82–3.45 (2H, m), 2.25 (3H, s), 1.90 (3H, s), 1.65–1.55 (2H, m), 1.37–1.32 (4H, m), 0.94–0.89 (3H, m).

Example 19

N-(2-Amino-5,6,7,8-tetrahydroquinazoline-4-yl)-N-pentylamine

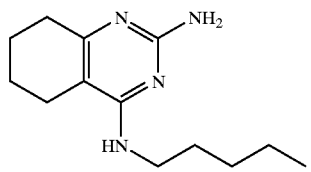

By using N-(2-chloro-5,6,7,8-tetrahydroquinazoline-4-yl)-N-pentylamine as a starting material and according to the method of Example 18, the object compound was obtained.

$^1$H-NMR (300 MHz, CDCl$_3$): δ 5.11 (2H, brs), 4.52 (1H, brs), 3.86–3.52 (2H, m), 2.57–2.54 (2H, m), 2.21–2.18 (2H, m), 1.83–1.75 (4H, m), 1.64–1.74 (2H, m), 1.40–1.30 (4H, m), 0.94–0.89 (3H, m).

Example 20

N-(2-Amino-6,7-dihydro-5H-cyclopenta[d]pyrimidine-4-yl)-N-pentylamine

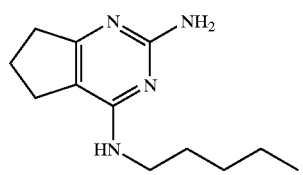

By using 2-chloro-N-pentyl-6,7-dihydro-5H-cyclopenta[d]pyrimidine-4-amine as a starting material and according to the method of Example 18, the object compound was obtained.

$^1$H-NMR (300 MHz, CDCl$_3$): δ 4.89 (2H, brs), 4.31 (1H, brs), 3.46–3.88 (2H, m), 2.75 (2H, t, J=7.7 Hz), 2.55 (2H, t, J=7.7 Hz), 2.07 (2H, tt, J=7.7,7.7 Hz), 1.64–1.54 (2H, m), 1.37–1.32 (4H, m), 0.94–0.89 (3H, m).

Example 21

2-(2-Amino-5,6,7,8-tetrahydroquinazoline-4-yl)amino]hexaneamide

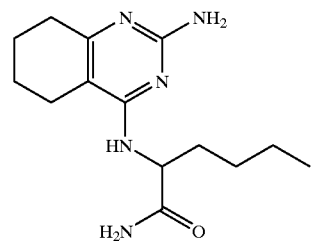

A mixture of methyl 2-[(2-amino-5,6,7,8-tetrahydroquinazoline-4-yl)amino]hexanoate (520 mg, 1.77 mmol) and 5M ammonia-ethanol (60 ml) was kept at 120° C. for 24 hours. The reaction mixture was concentrated in vacuo, purified by silica gel chromatography (20%MeOH/CHCl$_3$) to give the object compound (67.7 mg, 7.6%).

$^1$H-NMR (300 MHz, DMSO-d$_6$): δ 7.26 (1H, brs), 7.01 (1H, brs), 5.80 (1H, d, J=7.9 Hz), 5.58 (2H, brs), 4.46 (1H, dt, J=8.1, 7.9 Hz), 2.43–2.21 (4H, m), 1.85–1.56 (6H, m), 1.34–1.13 (4H, m), 0.92–0.77 (3H, m).

Example 22

N-(2-Amino-5-(2-methoxyethyl)-6-methylpyrimidine-4-yl)-N-pentylamine

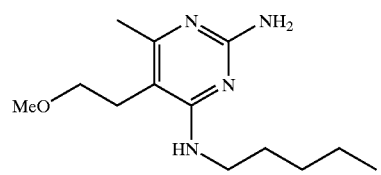

A mixture of 4-chloro-5-(2-methoxyethyl)-6-methylpyrimidine-2-ylamine (150 mg, 0.74 mmol), amylamine (0.86 ml) and dioxane (1.5 ml) was kept at 90° C. for 7 hours. The reaction mixture was concentrated in vacuo, and the residue was extracted with chloroform and a saturated aqueous NaHCO₃ solution. The organic layer was washed with saturated brine, dried over sodium sulfate, filtered and the filtrate was concentrated in vacuo. The residue was purified by column chromatography (4%MeOH: CHCl₃) to give the object compound (108 mg, 57.5%).

¹H-NMR (CDCl₃): δ 0.92 (3H, t, J=6.6), 1.40–1.32 (4H, m), 1.57 (2H, m), 2.21 (3H, s), 2.62 (2H, t, J=5.9), 3.31–3.38 (5H, m), 3.50 (2H, t, J=5.9), 4.72 (2H, brs), 5.62 (1H, m).

Example 23

3-[2-Amino-4-methyl-6-(pentylamino)pyrimidine-5-yl]propanenitrile

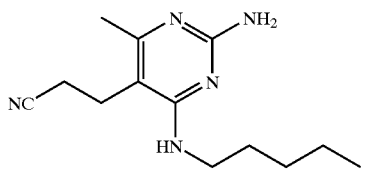

A mixture of 3-(2-amino-4-chloro-6-methylpyrimidine-5-yl)propanenitrile (500 mg, 2.54 mmol), amylamine (2.94 ml) and dioxane (5 ml) was kept at 90° C. for 8.5 hours. The procedure according to pro-treatment of Example 23 was carried out to give the object compound (346 mg, 55.0%).

¹H-NMR (CDCl₃): δ 0.92 (3H, t, J=6.9), 1.35 (4H, m), 1.60 (2H, m), 2.25 (3H, s), 2.45 (2H, t, J=7.9), 2.75 (2H, t, J=7.9), 3.40 (2H, m), 4.45 (1H, m), 4.65 (2H, brs).

Example 24

N-[2-Amino-5-ethyl-6-methylpyrimidine-4-yl)-N-pentylamine

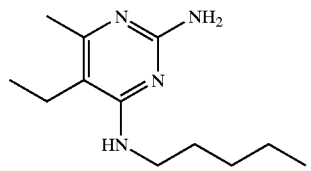

A mixture of 4-chloro-5-ethyl-6-methylpyrimidine-2-ylamine (400 mg,33 mmol), amylamine (1.35 ml) and dioxane (5 ml) was kept at 95–100° C. for 17 hours. The procedure according to pro-treatment of Example 23 was carried out to give the object compound (301 mg, 58.1%).

¹H-NMR (CDCl₃): δ 0.91 (3H, t, J=6.9), 1.06 (3H, t, J=7.6), 1.23–1.43 (4H, m), 1.59 (2H, m), 2.22 (3H, s), 2.35 (2H, q, J=7.6), 3.40 (2H, m), 4.50 (1H, m), 4.61 (2H, brs).

Example 25

According to the method of Example 23, the following compound was obtained:

1-[(2-Amino-5-butyl-6-methylpyrimidine-4-yl)amino]pentane-2-ol

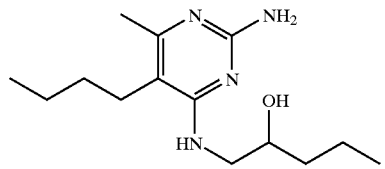

¹H-NMR (CDCl₃): δ 0.94 (6H, t), 1.45 (8H, m), 2.34 (3H, s), 2.37 (2H, m), 3.31 (1H, m), 3.48 (1H, s), 3.76 (2H, m), 6.10 (1H, brs), 6.32 (2H, brs).

Example 26

N-(2-Amino-5-benzyl-6-methylpyrimidine-4-yl)-N-pentylamine

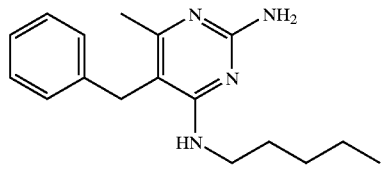

A mixture of 5-benzyl-4-chloro-6-methylpyrimidine-2-ylamine (500 mg, 2.14 mmol) , amylamine (1.24 ml ) and dioxane (4 ml ) was kept at 95–100° C. for 19 hours. The reaction mixture was concentrated in vacuo, and the residue was extracted with chloroform and a saturated aqueous NaHCO₃ solution. The organic layer was washed with saturated brine, dried over sodium sulfate, and concentrated in vacuo. The residue was purified by silica gel column chromatography (2%MeOH/CHCl₃) to give the object compound (546 mg, 89.7%).

¹H-NMR (CDCl₃): δ 0.81 (3H, t, J=7.3), 1.05 (2H, m), 1.19 (2H, m), 1.35 (2H, m), 2.28 (3H, s), 3.27 (2H, m), 3.76 (2H, s), 4.30 (1H, m), 4.64 (2H, brs), 7.12–7.31 (5H, m), 0.94–0.89 (3H, m).

Example 27

N-(2-Amino-5-benzylpyrimidine-4-yl)-N-pentylamine

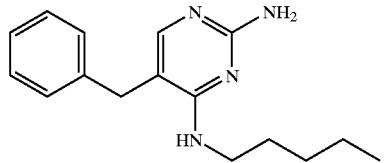

A mixture of 5-benzyl-4-chloropyrimidine-2-ylamine (350 mg, 0.74 mmol), amylamine (0.74 ml) and dioxane (4 ml) was kept at 90–100° C. for 8 hours. The reaction mixture was concentrated in vacuo, and the residue was extracted with ether and a saturated aqueous NaHCO₃ solution. The organic layer was washed with saturated brine, dried over sodium sulfate, filtered and concentrated. The residue was purified by silica gel column chromatography (MeOH:CHCl₃=70:1) to give the object compound (355 mg, 82.2%).

¹H-NMR (CDCl₃): δ 0.82 (3H, t, J=6.9), 1.04 (2H, m), 1.21 (2H, m), 1.35 (2H, m), 3.26 (2H, m), 3.66 (2H, s), 4.26 (1H, m), 4.64 (2H, brs), 7.16–7.33 (5H, m), 7.68 (1H, s).

Example 28

N-(2-Amino-5-phenethylpyrimidine-4-yl)-N-pentylamine

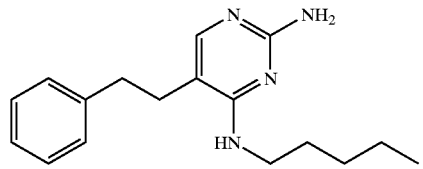

A mixture of 4-chloro-5-phenethylpyrimidine-2-ylamine (234 mg, 1 mmol), amylamine (0.58 ml) and dioxane (2 ml) was kept at 95–100° C. for 8.5 hours. The procedure according to pro-treatment of Example 27 was carried out to give the object compound (227 mg, 79.7%).

$^1$H-NMR (CDCl$_3$): δ 0.91 (3H, t, J=6.9), 1.25–1.42 (4H, m), 1.50 (2H, m), 2.55 (2H, t, J=7.3), 2.84 (2H, t, J=7.3), 3.31 (2H, m), 4.27 (1H, m), 4.60 (2H, brs), 7.15–7.33 (5H, m), 7.56 (1H, s).

Example 29

N-(2-Amino-5-benzyl-6-methylpyrimidine-4-yl)-N-pentane-2-ol

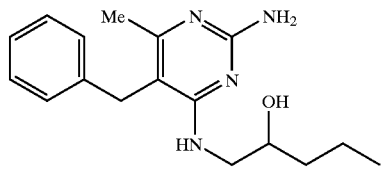

A mixture of 5-benzyl-4-chloro-6-methylpyrimidine-2-yl amine (1.5 g, 6.42 mmol), 2-hydroxypentylamine hydrochloride (990 mg, 7.06 mmol), triethylamine (1.4 g, 14.18 mmol) and diethyleneglycol diethyl ether (5 ml) was kept to warm for 15 hours in a bath (bath temperature: 90–100° C.). The solvent was removed in vacuo and the residue was purified by silica gel column chromatography (CHCl$_3$:MeOH:NH$_4$OHaq=100:10:0.4) to give the object compound (800 mg, 41.5%).

$^1$H-NMR (TMS/CDCl$_3$): d 0.86 (3H, t, J=6.9 Hz), 1.18–1.40 (4H, m), 2.27 (3H, s), 3.17–3.27 (1H, m), 3.60–3.71 (1H, m), 3.78 (2H, d, J=6.6 Hz), 4.76 (3H, br), 7.23 (2H, d, J=6.9 Hz), 7.28–7.33 (3H, m).

Example 30

The compounds in the following table can be prepared according to the methods of the above Examples.

| No. | R1 | R2 | R3 |
|---|---|---|---|
| 1 | 4-methyl-4-ethyl-tetrahydropyran-4-carbonyl | —Me | —(CH$_2$)$_3$Me |
| 2 | 4-methyl-4-ethyl-tetrahydropyran-4-carbonyl | —Me | 3-fluorophenethyl |
| 3 | 4-methyl-4-ethyl-tetrahydropyran-4-carbonyl | —Me | —CH$_2$CH$_2$CN |
| 4 | 4-methyl-4-ethyl-tetrahydropyran-4-carbonyl | —Me | —CH$_2$CH$_2$CONH$_2$ |
| 5 | 4-methyl-4-ethyl-tetrahydropyran-4-carbonyl | —Me | cyclohexylmethyl |
| 6 | 4-methyl-4-ethyl-tetrahydropyran-4-carbonyl | —Me | 4-pyridylmethyl |
| 7 | 4-methyl-4-ethyl-tetrahydropyran-4-carbonyl |  | —(CH$_2$)$_4$— |

-continued

| No. | R1 | R2 | R3 |
|---|---|---|---|
| 8 | —(CH$_2$)$_4$Me | —Me | —CH$_2$CH$_2$NHSO$_3$Me |
| 9 | —(CH$_2$)$_4$Me | —Me | 3-ethylbenzamide (N-methyl) group |
| 10 | —(CH$_2$)$_4$Me | —Me | —(CH$_2$)$_3$NH$_2$ |
| 11 | —(CH$_2$)$_4$Me | —Me | —CH$_2$CH$_2$CONH$_2$ |
| 12 | —(CH$_2$)$_4$Me | —Me | 3-methylfuran group |
| 13 | —(CH$_2$)$_4$Me | —Et | 3-methylfuran group |
| 14 | —(CH$_2$)$_4$Me | —(CH$_2$)$_3$— | |
| 15 | 4-methyl-tetrahydropyran-4-yl (Bu) | —Me | —(CH$_2$)$_3$Me |
| 16 | 4-methyl-tetrahydropyran-4-yl (Bu) | —Me | 2-methoxybenzyl |
| 17 | 4-methyl-tetrahydropyran-4-yl (Bu) | —Me | —CH$_2$CH$_2$CN |
| 18 | 4-methyl-tetrahydropyran-4-yl (Bu) | —Me | —CH$_2$CH$_2$CONH$_2$ |
| 19 | 4-methyl-tetrahydropyran-4-yl (Bu) | —Me | cyclohexylmethyl |
| 20 | 4-methyl-tetrahydropyran-4-yl (Bu) | —Me | 3-pyridylmethyl |
| 21 | 4-methyl-tetrahydropyran-4-yl (Bu) | —(CH$_2$)$_3$— | |
| 22 | 1-hydroxy-3-methoxy-2-methylpropyl | —Me | —(CH$_2$)$_3$Me |
| 23 | 1-hydroxy-3-methoxy-2-methylpropyl | —Me | 4-fluorobenzyl |
| 24 | 1-hydroxy-3-methoxy-2-methylpropyl | —Me | —CH$_2$CH$_2$CN |
| 25 | 1-hydroxy-3-methoxy-2-methylpropyl | —Me | —CH$_2$CH$_2$CONH$_2$ |
| 26 | 1-hydroxy-3-methoxy-2-methylpropyl | —Me | cyclohexylmethyl |
| 27 | 1-hydroxy-3-methoxy-2-methylpropyl | —(CH$_2$)$_4$— | |

Reference Example 1

4-Chloro-5,6,7,8-tetrahydroquinazoline-2-ylamine (1-1) 2-Amino-5,6,7,8-tetrahydroquinazoline-4-ol To a solution of ethyl 2-oxocyclohexane carboxylate (41 g, 241 mmol) in ethanol (200 ml) was added guanidine carbonate (26.0 g, 289 mmol) under stirring at room temperature. The reaction mixture was refluxed for 1 hour and then cooled to room temperature. The precipitated crystals were filtered and washed with water, followed with methanol. The crystals were dried in vacuo to give the object compound (35.5 g, 89%).

$^1$H-NMR (300 MHz, DMSO-d$_6$): δ 10.64 (1H, brs), 6.18 (2H, brs), 2.35–2.25 (2H, m), 2.23–2.15 (2H, m), 1.70–1.54 (4H, m).

(1-2) 4-Chloro-5,6,7,8-tetrahydroquinazoline-2-ylamine

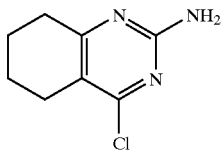

To a suspension of 2-amino-5,6,7,8-tetrahydroquinazoline-4-ol (20.0 g, 121 mmol) in toluene (150 ml) was dropped phosphorus oxychloride (55.7 g, 363 mmol) at 90° C. The mixture was stirred for 1 hour and the solvent was removed in vacuo. The residue was poured into 28% aqueous ammonia solution at 0° C. The solid was filtered and purified by silica gel column chromatography (3%MeOH/CHCl$_3$) to give the object compound (13.5 g, 60%).

$^1$H-NMR (300 MHz, DMSO-d$_6$): δ 6.69 (2H, brs), 2.60–2.52 (2H, m), 2.52–2.44 (2H, m), 1.76–1.66 (4H, m).

$^{13}$C NMR (75 Hz, DMSO-d$_6$): δ 168.4, 161.0, 160.1, 114.8, 31.8, 24.3, 22.1, 21.7.

Reference Example 2

5-Butyl-4-chloro-6-methylpyrimidine-2-ylamine (2-1) 2-Amino-5-butyl-6-methylpyrimidine-4-ol

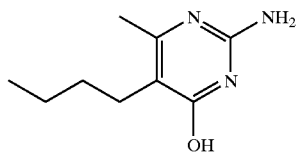

A mixture of ethyl 2-acetylhexanoate (5.59 g, 30 mmol), guanidine carbonate (6.49 g, 30 mmol) and ethanol (20 ml) was refluxed for 11 hours and then ice-cooled. The precipitated crystals were filtered, washed with ethanol and dried in vacuo to give 2-amino-5-butyl-6-methylpyrimidine-4-ol (2.59 g, 47%).

(2-2) 5-Butyl-4-chloro-6-methylpyrimidine-2-ylamine

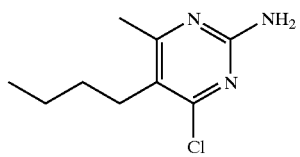

2-Amino-5-butyl-6-methylpyrimidine-4-ol (1.0 g, 5.52 mmol) and phosphorus oxychloride (12 ml) were refluxed for 3 hours. The solvent was removed in vacuo and the residue was purified by silica gel column chromatography (n-hexane: ethyl acetate=2:1) to give the object compound (325 mg, 29%).

$^1$H-NMR(CDCl$_3$): δ 0.96 (3H, t, J=7.1 Hz), 1.37–1.50 (4H, m), 2.38 (3H, s), 2.60 (2H, m), 5.01 (2H, brs).

Reference-Example 3

4-Chloro-5-hexyl-6-methylpyrimidine-2-ylamine

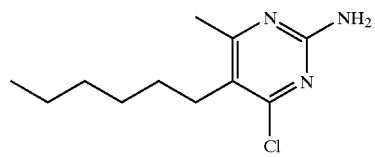

By using ethyl 2-acetyloctanoate (6.43 g, 30 mmol) as a starting material and according to the method of Reference-example 2, there was obtained 2-amino-5-hexyl-6-methylpyrimidine-4-ol (4.70 g, 74%). By reacting the obtained 2-amino-5-hexyl-6-methylpyrimidine-4-ol (1 g, 4.78 mmol) and phosphorous oxychloride (12 ml), there was obtained the object compound (196 mg, 18%).

$^1$H-NMR(CDCl$_3$): δ 0.90 (3H, t, J=6.8 Hz), 1.31–1.52 (8H, m), 2.37 (3H, s), 2.59 (2H, m), 4.95 (2H, brs).

Reference-Example 4

4-Chloro-7,8-dihydro-5H-pyrano[4,3-d]pyrimidine-2-ylamine (4-1) 2-Amino-7,8-dihydro-5H-pyrano[4,3-d]pyrimidine-4-ol

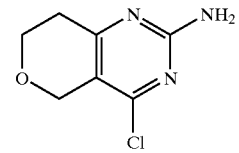

By using ethyl 4-oxotetrahydoro-2H-pyran-3-carboxylate (600 mg, 3.49 mmol) as a starting material and according to the method of Reference-example 2, there was obtained 2-amino-7,8-dihydro-5H-pyrano[4,3-d]pyrimidine-4-ol (230 mg, 39%).

$^1$H-NMR (300 MHz, DMSO-d$_6$): δ 10.78 (1H, brs), 6.34 (2H, brs), 4.24 (2H, brs), 3.78 (2H, t, J=5.5 Hz), 2.36 (2H, t).

(4-2) 4-Chloro-7,8-dihydro-5H-pyrano[4,3-d]pyrimidine-2-ylamine

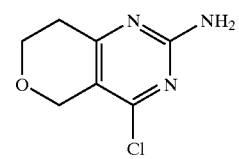

By reacting 2-amino-7,8-dihydro-5H-pyrano[4,3-d]pyrimidine-4-ol (562 mg, 3.36 mmol) and phosphorous oxychloride (3 ml), there was obtained the object compound (136 mg, 22%).

$^1$H-NMR (300 MHz, CDCl$_3$): δ 5.10 (1H, brs), 4.62 (2H, s), 3.99 (2H, t, J=5.4 Hz), 2.78 (2H, t, J=5.4 Hz).

Reference-Example 5

4-Butyl-6-chloro-5-methylpyrimidine-2-ylamine (5-1) 2-Amino-6-butyl-5-methylpyrimidine-4-ol

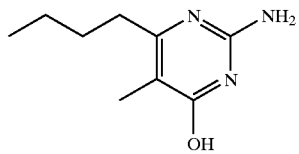

By using ethyl 2-methyl-3-oxoheptanoate (1.06 g, 5.69 mmol) as a starting material and according to the method of Reference-example 2, there was obtained 2-amino-6-butyl-5-methylpyrimidine-4-ol (420 mg).

$^1$H-NMR (DMSO-$d_6$): δ 0.88 (3H, t, J=7.3 Hz), 1.30 (2H, m), 1.49 (2H, m), 1.78 (3H, s), 2.32 (2H, t, J=7.3 Hz), 6.18 (2H, bs), 10.69 (1H, bs).

(5-2) 4-Butyl-6-chloro-5-methylpyrimidine-2-ylamine

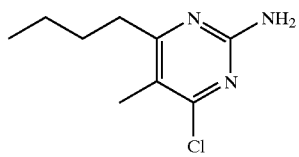

By reacting 2-amino-6-butyl-5-methylpyrimidine-4-ol (0.82 g, 4.52 mmol) and phosphorous oxychloride (10 ml), there was obtained the object compound (720 mg).

$^1$H-NMR (CDCl$_3$): δ 0.93 (3H, t, J=7.3 Hz), 1.40 (2H, m), 1.60 (2H, m), 2.20 (3H, s), 2.63 (2H, t, J=7.3 Hz), 5.73 (2H, bs).

Reference-Example 6

4-Chloro-5-(2-methoxyethyl)-6-methlpyrimidine-2-ylamine (6-1) 2-Amino-5-(2-methoxyethyl)-6-methlpyrimidine-4-ol

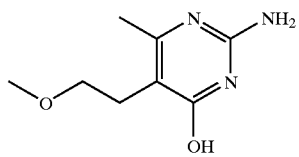

A mixture of ethyl 2-(2-methoxyethyl)-3-oxobutanoate (4 g, 21 mmol), guanidine carbonate (2.27 g, 16.3 mmol) and ethanol (16 ml) was refluxed for 9 hours. After cooling, the precipitate was filtered and washed with water, ethanol and ether in order, to give the object compound (1.24 g, 31.9%)

$^1$H-NMR (DMSO-$d_6$): δ 2.06 (3H, s), 2.49–2.54 (4H(2H), m, overlapped with DMSO), 3.22 (3H, s), 3.28 (2H, t, J=7.3), 6.40 (2H, brs), 10.90 (1H, brs).

(6-2) 4-Chloro-5-(2-methoxyethyl)-6-methylpyrimidine-2-ylamine

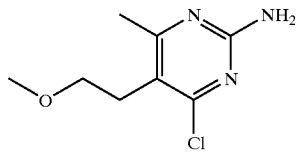

A mixture of 2-amino-5-(2-methoxyethyl)-6-methylpyrimidine-4-ol (600 mg, 3.27 mmol) and phosphorus oxychloride (6 ml) was kept at 90° C. for 5.5 hours. The reaction mixture was concentrated in vacuo. Was added to the residue and an aqueous ammonia solution was cautiously added. The mixture was extracted with chloroform and the organic layer was washed with saturated brine, dried over sodium sulfate and the solvent was concentrated. The residue was purified by silica gel column chromatography (chloroform: ethyl acetate=8:2) to give the object compound (200 mg, 30.3%).

$^1$H-NMR(CDCl$_3$): δ 2.42 (3H, s), 2.91 (2H, t, J=7.3), 3.34 (3H, s), 3.51 (2H, t, J=7.3), 5.03 (2H, brs).

Reference-Example 7

3-(2-Amino-4-chloro-6-methlpyrimidine-5-yl)propanenitrile (7-1) 3-(2-Amino-4-hydroxy-6-methlpyrimidine-5-yl)propanenitrile

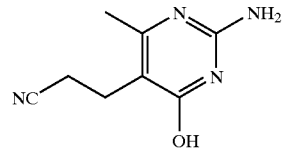

A mixture of ethyl 2-(2-cyanoethyl)-3-oxobutanoate (9 g, 49 mmol), guanidine carbonate (5.30 g, 29.4 mmol) and pyridine (49 ml) was kept at 100° C. for 8 hours. The procedure according to pro-treatment of Reference-example 6 was carried out to give the object compound (3.38 g, 38.6%).

$^1$H-NMR (DMSO-$d_6$): δ 2.11 (3H, s), 2.58 (4H, s), 6.44 (2H, brs), 10.91 (1H, brs).

(7-2) 3-(2-Amino-4-chloro-6-methlpyrimidine-5-yl)propanenitrile

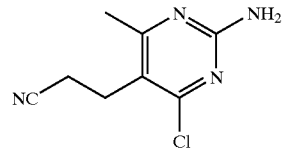

A mixture of 3-(2-amino-4-hydroxy-6-methylpyrimidine-5-yl)propanenitrile (2 g, 11.2 mmol) and phosphorous oxychloride (13 ml) was kept at 90° C. for 5 hours. The procedure according to pro-treatment of Reference-example 6 was carried out to give the object compound (1.06 g, 48%).

$^1$H-NMR (CDCl$_3$): δ 2.47 (3H, s), 2.61 (2H, t, J=7.6), 3.02 (2H, t, J=7.6), 5.11 (2H, brs).

Reference-Example 8

4-Bromo-5,6,7,8-tetrahydroquinazoline-2-ylamine

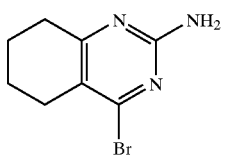

To a suspension of 2-amino-5,6,7,8-tetrahydroquinazoline-4-ol (1.65 g, 10 mmol) in toluene (16.5 ml) was added phosphorous oxybromide (3 g) and the mixture was kept to warm in a bath (bath temperature 90–100° C.) for 2 hours. After confirming disappearance of the starting materials, the reaction mixture was poured into ice-water, and was extracted with chloroform and a saturated aqueous NaHCO$_3$ solution. The organic layer was washed with saturated brine, dried over sodium sulfate, filtered and concentrated in vacuo. The residue was purified by silica gel column chromatography (CHCl$_3$) to give the object compound (1.7 g, 75%).

$^1$H-NMR (300 MHz, CDCl$_3$): δ 5.13 (2H, brs), 2.66 (2H, brm), 2.57 (2H, brm), 1.77–1.82 (4H, m).

Reference-Example 9

2-Chloro-N-pentyl-6,7-dihydro-5H-cyclopenta [d] pyrimidine-4-amine (9-1) 2,4-Dichloro-6,7-dihydro-5H-cyclopenta[d]-pyrimidine

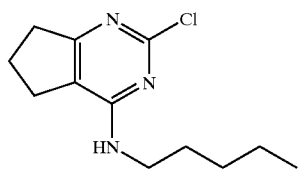

6,7-Dihydro-5H-cyclopenta [d]pyrimidine-2,4-diol (359 mg) and phosphorous oxychloride (5 ml) were refluxed for 3 hours. After the reaction, the mixture was concentrated in vacuo. The residue was poured into water and extracted with chloroform. The organic layer was washed with saturated brine, dried over sodium sulfate and concentrated in vacuo to give 2,4-dichloro-6,7-dihydro-5H-cyclopenta[d] pyrimidine (410 mg).

(9-2) 2-Chloro-N-pentyl-6,7-dihydro-5H-cyclopenta[d] pyrimidine-4-amine

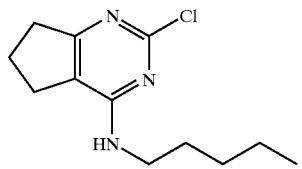

A mixture of 2,4-dichloro-6,7-dihydro-5H-cyclopenta[d] pyrimidine (410 mg) and pentylamine (1 ml) were stirred at room temperature for 8 hours. The reaction mixture was poured into an aqueous ammonium chloride solution and the solution was extracted with chloroform. The organic layer was washed with saturated brine, dried over sodium sulfate and concentrated in vacuo to give the object compound (296 mg, 65%).

$^1$H-NMR (300 MHz, CDCl$_3$): δ 4.56 (1H, brs), 3.52–3.46 (2H, m), 2.86 (2H, t, J=7.5 Hz), 2.63 (2H, t, J=7.5 Hz), 2.13 (2H, tt, J=7.5,7.5 Hz), 1.66–1.57 (2H, m), 1.40–1.33 (4H, m), 0.94–0.89 (3H, m).

Reference-Example 10

N-(2-Chloro-5,6,7,8-tetrahydroquinazoline-4-yl)-N-pentylamine

The above compound was prepared according to the method of Reference-Example 9.

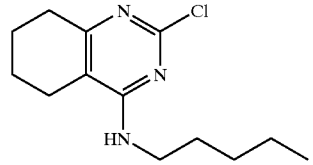

$^1$H-NMR (300 MHz, CDCl$_3$): δ 4.64 (1H, brs), 3.51–3.45 (2H, m), 2.68–2.65 (2H, m), 2.27–2.23 (2H, m), 1.90–1.75 (4H, m), 1.70–1.55 (2H, m), 1.45–1.30 (4H, m), 0.93–0.89 (3H, m).

Reference-Example 11

N-(2-Chloro-5,6-dimethylpyrimidine-4-yl)-N-pentylamine

The above compound was prepared according to the method of Reference-example 9.

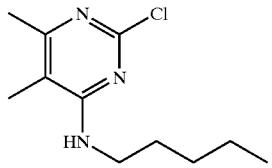

$^1$H-NMR (300 MHz, CDCl$_3$): δ 4.65 (1H, brs), 3.51–3.44 (2H, m), 2.34 (3H, s), 1.97 (3H, s), 1.70–1.55 (2H, m), 1.45–1.30 (4H, m), 0.94–0.89 (3H, m).

Reference-Example 12

2-Amino-5-benzyl-6-methylpyrimidine-4-ol

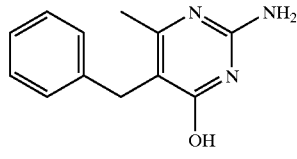

A mixture of ethyl 2-benzyl-3-oxobutanoate (6 g, 27.2 mmol), guanidine carbonate (2.94 g, 16.3 mmol) and ethanol (20 ml) was refluxed for 10 hours. After cooling, the precipitate was filtered and washed with water, ethanol and ether in order, to the object compound (3.62 g, 61.7%).

$^1$H-NMR (DMSO-d$_6$): d 2.01 (3H, s), 3.64 (2H, s), 6.39 (3H, brs), 7.10–7.26 (5H, m), 10.89 (1H, brs).

Reference-Example 13

5-Benzyl-4-chloro-6-methylpyrimidine-2-ylamine

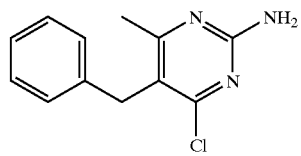

A mixture of 2-amino-5-benzyl-6-methylpyrimidine-4-ol (1.2 g, 5.57 mmol) and phosphorous oxychloride (9 ml) was kept to warm at 90° C. for 6 hours. The reaction mixture was concentrated in vacuo. Ice-water was added to the residue and an aqueous ammonia was cautiously added thereto. The solution was extracted with chloroform. The organic layer was washed with saturated brine, dried over sodium sulfate and concentrated in vacuo. The residue was purified by silica gel column chromatography (chloroform: ethyl acetate=8:2) to give the object compound (700 mg, 53.7%).

$^1$H-NMR(CDCl$_3$): d 2.30 (3H, s) 4.05 (2H, s). 5.07 (2H, brs), 7.10–7.31 (5H, m).

Reference-Example 14

2-Amino-5-phenethylpyrimidine-4-ol

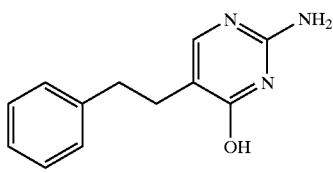

Metallic sodium (966 mg, 42 mmol) was added to ether (42 ml) under nitrogen gas. Thereto a mixture of 4-phenylbutyric acid ethyl ester (8 g, 42 mmol) and ethyl formate (3.42 g, 42 mmol) was dropped under stirring at room temperature over a 30 minute period. The mixture was stirred for 10 hours to prepare a ketoester compound.

Then, sodium ethoxide (3.14 g, 46.2 mmol) was added to ethanol (42 ml) under nitrogen gas. Thereto guanidine hydrochloride (4.41 g, 46.2 mmol) was added and the mixture was stirred for 30 minutes. The salt was filtered off and the filtrate was added to the ketoester compound in ether previously prepared. The reaction mixture was kept at 80–90° for 6 hours. After reaction, the solvent was removed in vacuo. A 10% aqueous citric acid solution was added to the residue to adjust pH to 8. Ethyl acetate was added to the mixture and the resulting insoluble material was filtered, washed with ethanol and ether to give the object compound (853 mg, 9.5%).

$^1$H-NMR(DMSOd$_6$): d 2.46 (2H, t, J=7.3), 2.73 (2H, t, J=7.3), 6.32 (2H, brs), 7.16–7.29 (5H, m), 10.88 (1H, brs).

Reference-Example 15

4-Chloro-5-phenethylpyrimidine-2-ylamine

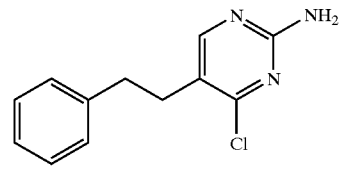

A mixture of 2-amino-5-phenethylpyrimidine-4-ol (600 mg, 2.79 mmol) and phosphorous oxychloride (5 ml) was kept to warm at 90° C. for 6 hours. The reaction mixture was condensed in vacuo. Ice-water was added to the residue and an aqueous ammonia was cautiously added thereto. The solution was extracted with chloroform. The organic layer was washed with saturated brine, dried over sodium sulfate and concentrated in vacuo. The residue was purified by silica gel column chromatography (chloroform: ethyl acetate=8:2) to give the object compound (265 mg, 40.7%).

$^1$H-NMR(CDCl$_3$): d 2.87 (4H, s), 5.08 (2H, brs), 7.15–7.32 (5H, m), 7.90 (1H, s).

Reference-Example 16

5-Benzyl-4-chloropyrimidine-2-ylamine

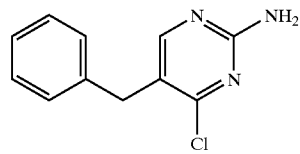

The above compound was prepared according to the method described in J. Amer. Chem. Soc., 73, 3758–3762 (1951).

Test 1

Activity on Cytokines Production From Mouse Lymph Node Cells by Compounds of Working Examples Experimental Method 1) Animals BALB/c mice were purchased from Japan Charlse River (Yokohama) and 8 weeks female mice were used.

2) Culture Medium

D-MEM (High Glucose) medium (Nikken Biomedical Research Lab. (Kyoto), Code No. CM4402) supplemented with 20% heat-inactivated (56° C., 30 min.) fetal bovine serum (Characterized, Code No. A-1115-L, HyClone Lab., Logan, Utah), 50 µM 2-mercaptoethanol (Sigma, St. Louis, Mo., Code No. M-6250), 100 unit/ml penicillin and 100 µg/ml streptomycin (Penicillin-Streptomycin, Bibco-BRL, Code No. 15140–122) were used for the assay.

3) Test Compounds

Each test compound dissolved in DMSO (Nacalai Tesque (Kyoto) code No. 11J) at a concentration of 100 mM was diluted to final concentration with the medium.

4) Sensitization and Preparation of Lymph Node Cells

KLH (0.2 mg) was subcutaneously administered to mouse foot with Freund's complete adjuvant (Difco Lab., Detroit, Mich., Code No. 3113-60-5). Eight days later popliteal lymph node was picked up and its cell suspension was prepared.

5) Production of Cytokine by Stimulation with an Antigen

KLH (0.1 mg/ml) and the test compound were added to lymph node cells ($2.5 \times 10^6$ cells/ml) and the mixture was incubated at 37° C. under 5% $CO_2$ for 4 days (Corning 25850, 0.15 ml/well). Then, amount of cytokine produced in the supernatant was measured by ELISA specific to cytokine.

Amounts of interleukin 4 (IL-4) and interleukin 5 (IL-5) as a typical Th2 type cytokine, and amount of interferon γ (IFN-γ) as a typical Th1 type cytokine were measured.

6) Method of Measurement (ELISA)

Amount of IL-4 was measured by ELISA as mentioned below. A rat anti-mouse IL-4 antibody (Pharmingen, San Diego, Calif., Code No. 18031D, 0.5 mg/ml) as a primary antibody was diluted 250 times with hydrogen carbonate buffer, and it was inoculated to the 96-well plate (Falcon 3912, Becton Dickinson and Company, Flanklin Lakes, N.J.) (50 /well) and each well was coated at 4° C. overnight. Then the plate was blocked with PBS (–) solution (phosphate-buffered saline without calcium chloride and magnesium chloride) containing 3% BSA (200 μl/well). After rinsing the plate three times with PBS (–) solution containing 0.05% polyoxyethylene solbitan monolaurate (Tween 20™, Nacalai Tesque (Kyoto) Code No. 281-51) (PBST), the supernatant of the culture medium was added to the wells (50 μl/well) and incubated at room temperature for 4 hours. Recombinant mouse IL-4 (Pharmingen, Code No. 19231W) was used for preparing a calibration curve.

After rinsing the plate three times with PBST, a rat anti-mouse IL-4 antibody labeled by biotin (Pharmingen, Code No. 18042D, 0.5 mg/ml) as a secondary antibody, which was diluted 500 times with PBS (–) solution containing 0.1% BSA, was poured into wells (100 μl/well). The plate was incubated at room temperature for one hour. The secondary antibody bound to the plate was detected with streptoabidin alkaliphosphatase (Kirkegaad & Perry Lab., Gaithersburg, MD, Code No. 15-30-00) (0.25 μg/ml, 100 μl/well). After incubation of the plate at 37° C. for one hour and rinsing the plate three times with PBST, the coloring was done by adding PNPP substrate (p-nitrophenyl disodium phosphate substrate (Nacalai Tesque) (1 mg/ml, 1001 μl/well)). The absorption at 415 nm was measured by a microplate reader (MTP-120 Microplate reader, Corona Electric Co.)

Measurement of amount of IFNγ was carried out in the same method as mentioned above by using a rat anti-mouse IFNγ antibody (Pharmingen, San Diego, Calif., Code No. 18181D, 0.5 mg/ml) as a primary antibody and a rat anti-mouse IL-5 antibody labeled by biotin (Pharmingen, Code No. 18112D, 0.5 mg/ml) as a secondary antibody. Recombinant mouse IFN-γ (Pharmingen, Code No. 19301U) was used for preparing a calibration curve.

Measurement of amount of IL-5 was carried out in the same method as mentioned above by using a rat anti-mouse IL-5 antibody (Pharmingen, San Diego, Calif., Code No. 18051D, 0.5 mg/ml) as a primary antibody and a rat anti-mouse IL-5 antibody labeled by biotin (Pharmingen, Code No. 18062D, 0.5 mg/ml) as a secondary antibody. Recombinant mouse IL-5 (Pharmingen, Code No. 19241W) was used for preparing a calibration curve. The test was carried out three times and their average was calculated.

7) Results

Compounds of examples 10, 11, 14, 19 and 25 were used as test compounds in this test.

Every compound was confirmed to inhibit the production of IL-4 and IL-5 and to enhance the production of IFN-γ.

Test 2

Activity on Cytokines Production From Mouse Lymph Node Cells by the Compounds of Working Examples Experimental Method In the same manner as in Test 1, each test compound dissolved in DMSO (Nacalai Tesque (Kyoto) code No. 11J) at a concentration of 100 mM was diluted to final concentration with the medium. Sensitization and preparation of lymph node cells, production of cytokine by stimulation with an antigen and measurement of amounts of cytokines were conducted in the same method as in Test 1.

By measuring inhibition rate of production of IL-4 at various concentrations of each test compound and using a graph relating to the compound concentration and the inhibition rate, 50% inhibition concentration ($IC_{50}$) on each test compound was calculated.

The results were shown in Table 1.

TABLE 1

| Ex. No. | IL-4 inhibition activity $IC_{50}$ (μg/ml) | Ex. No. | IL-4 inhibition activity $IC_{50}$ (μg/ml) |
|---|---|---|---|
| 1 | 0.6 | 2 | 0.6 |
| 3 | 0.5 | 4 | 3 |
| 5 | 0.2 | 6 | 1 |
| 7 | 0.5 | 8 | 1 |
| 9 | 1 | 10 | 0.1 |
| 11 | 0.1 | 12 | 1 |
| 13 | 10 | 14 | 0.1 |
| 15 | 0.4 | 16 | 3 |
| 17 | 5 | 18 | 0.3 |
| 19 | 0.2 | 20 | 0.3 |
| 21 | 0.5 | 22 | 0.5 |
| 23 | 0.5 | 24 | 0.2 |
| 25 | 0.1 | | |

Test 3

Activity on Cytokines Production From Mouse Lymph Node by Compounds of Working Examples Experimental Method and Results In the same manner as in Test 1, each test compound dissolved in DMSO (Nacalai Tesque (Kyoto) code No. 11J) at a concentration of 100 mM was diluted to final concentration the medium. Sensitization and preparation of lymph cells, production of cytokine by stimulation with an en and measurement of amounts of cytokines were conducted in the same method as in Test 1.

As results, compounds of examples 26, 27 and 28 were confirmed to inhibit the production of IL-4 and IL-5 and to enhance the production of IFN-γ.

Test 4

Activity on Cytokines Production From Mouse Lymph Node Cells by Compounds of Working Examples Experimental Method and Results In the same manner as in Test 1, each test compound dissolved in DMSO (Nacalai Tesque (Kyoto) code No. 11J) at a concentration of 100 mM was diluted to final concentration with the medium. Sensitization and preparation of lymph node cells, production of cytokine by stimulation with an antigen and measurement of amounts of cytokines were conducted in the same method as in Test 1.

By measuring inhibition rate of production of IL-4 at various concentrations of each test compound and using a graph relating to the compound concentration and the inhibition rate, 50% inhibition concentration ($IC_{50}$) on each test compound was calculated.

The results were shown in Table 2.

TABLE 2

| Ex. No. | IL-4 inhibition activity $IC_{50}$ (μg/ml) |
|---|---|
| 26 | 0.5 |
| 27 | 1 |
| 28 | 2 |

Test 5

Activity on IgE Production From Mouse In Vivo by Compounds of Working Examples

Experimental Method

1) Animal

BALB/c mice (8 weeks female mice) were purchased from Japan Charles River (Yokohama) and after pre-feeding for 9 days the mice were used.

2) Sensitization with Ovalbumin

Physiological saline solution containing ovalbumin (Sigma Chemical Co., St Louis, Mo.) (4 μg/ml) and aluminum hydroxide-adjuvant (Alu-Gel-S; Serva Feinbiochemica GmbH & Co., Code No. 12261) were mixed in the same amount and the mixture was intraperitoneally administered to mouse.

3) Administration Method of Test Compound

The test compound was suspended in methylcellulose, and the suspension was administered one hour before the sensitization with ovalubmin and once a day for 12 days after the sensitization. Methylcellulose was used as a control.

4) Taking Blood and Preparing Serum

On 13th day after the sensitization blood was taken from orbital veniplex under anesthesia with a heparin treated capillary and centrifuged to prepare serum.

5) Measurement of IgE in Blood

Measurement of IgE in blood was carried out by ELISA. By using a rat anti-mouse IgE monoclonal antibody (Yamasa soy sauce Co., Chiba, Code No. 7627) as a primary antibody and a biotin labeled rat anti-mouse IgE monoclonal antibody (Yamasa soy sauce Co., Chiba, Code No. 7617), the measurement of amount of IgE was carried out in the same method as in Test 2. The assay was done using the serum 500 times. Amount of IgE in blood was calculated by using standard curve of mouse IgE (Yamasa soy sauce Co., Chiba, Code No. 7626).

6) Statistic Dealing

The result was statistically dealt with t-calibration or Welch calibration.

Test6

Activity Against Contact Hypersensitivity Reaction Induced by TNCB

Test Method

BALB/c mice (6–8 weeks female mice) were purchased from Japan Charlse River (Yokohama). Before use, the mice were allowed to acclimatize for one week.

2) Sensitization

Hair on mouse abdomen was cut and thereon was spread 7% 2,4,6-trinitrochlorobenzene (TNCB) in acetone (0.1 ml/mouse) to sensitize.

3) Method of Measurement of Thickness of Auricula

Six days after sensitization, 1% TNCB solution in acetone was spread on both sides of left auricula for induction. Twenty four hours later thickness of auliculae was measured.

Value of thickness of auricula=thickness of spread left auricula—thickness of unspread right auricula.

4) Administration Method of Test Compound

The solution prepared by dissolving a test compound (0.4 mg) in acetone (20 μl) was spread on left auricula 1–2 hours before sensitization.

INDUSTRIAL APPLICABILITY

The pyrimidine derivatives or salts thereof of the present invention show the activities that enhance immune responses on Th1 and suppress the immune responses on Th2 simultaneously and further, control the immune responses by changing the balance of Th1 and Th2. For example, they enhance production of Th1 type cytokines such as IFN-γ, etc. and inhibit production of Th2 type cytokines such as IL-4, IL-5, etc. Due to these activities, they can be used as therapeutic and prophylactic agents for allergic diseases, parasitism, autoimmune diseases such as systemic lupus erythemathosus, virus or bacteria infectious diseases, malignant tumor, and acquired immunodeficiecy syndrome (aids).

What is claimed is:

1. A pyrimidine compound of the formula (1) or its salt

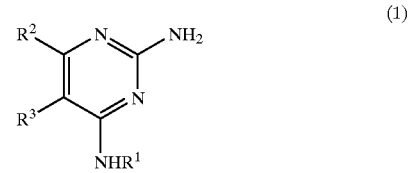

(1)

wherein $R^1$ is a formula (2)

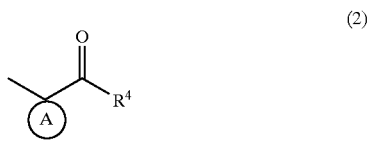

(2)

wherein ring A is substituted or unsubstituted $C_{3-10}$ cycloalkane, substituted or unsubstituted $C_{5-10}$ cycloalkene, substituted or unsubstituted $C_{7-10}$ bicycloalkane, or substituted or unsubstituted heterocyclic ring having an O atom or a S atom as a heteroatom, and said S atom may form sulfinyl or sulfonyl together with one or two oxygen atoms, and $R^4$ is straight or branched $C_{1-10}$ alkyl, $C_{2-6}$ alkenyl, $C_{3-6}$ alkinyl, $C_{3-6}$ cycloalkyl, $C_{4-10}$ cycloalkyl-alkyl, or $OR^8$, wherein $R^8$ is straight or branched $C_{-1-10}$ alkyl, $C_{3-6}$ alkenyl, $C_{3-6}$ alkinyl, $C_{3-6}$ cycloalkyl or $C_{4-10}$ cycloalkyl-alkyl, or $R^1$ is a formula (3)

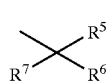

wherein
- $R^5$ is straight or branched $C_{2-10}$ alkyl; $C_{2-6}$ alkenyl; $C_{3-6}$ alkinyl; straight or branched $C_{1-10}$ alkyl substituted by hydroxy, halogen atom or $C_{1-4}$ alkoxy; $C_{3-8}$ cycloalkyl; a 5 to 7 membered saturated heterocyclic ring having one or two oxygen atoms as heteroatoms; or $C(=O)R^9$, wherein $R^9$ is straight or branched $C_{1-10}$ alkyl, $C_{2-6}$ alkenyl, $C_{3-6}$ alkinyl, $C_{3-6}$ cycloalkyl, $C_{4-10}$ cycloalkyl-alkyl, or $OR^{10}$, wherein $R^{10}$ is straight or branched $C_{1-10}$ alkyl, $C_{2-6}$ alkenyl, $C_{3-6}$ alkinyl, $C_{3-6}$ cycloalkyl or $C_{4-10}$ cycloalkyl-alkyl,
- $R^6$ is a hydrogen atom, straight or branched $C_{1-10}$ alkyl, $C_{6-10}$ aryl, halogen atom, $C_{6-10}$ aryl substituted by $C_{1-4}$ alkoxy or $C_{1-4}$ alkyl, carbamoyl, or hydroxymethyl, and
- $R^7$ is a hydrogen atom, or straight or branched $C_{1-10}$ alkyl, and
- $R^2$ and $R^3$ taken together are $C_{3-5}$ alkylene or said alkylene in which methylene is substituted by an O atom.

2. The pyrimidine compound or its pharmaceutically acceptable salt of claim 1, wherein $R^2$ and $R^3$ taken together are trimethylene or tetramethylene.

3. The pyrimidine compound or its pharmaceutically acceptable salt of claim 1, wherein $R^1$ is the formula (2)

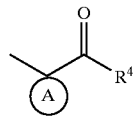

wherein ring A and $R^4$ are the same as defined above.

4. The pyrimidine compound or its pharmaceutically acceptable salt of claim 1, wherein $R^1$ is the formula (3)

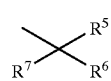

wherein $R^5$, $R^6$ and $R^7$ are the same as defined above.

5. The pyrimidine compound or its pharmaceutically acceptable salt of claim 1 or 4, wherein $R^5$ is straight $C_{3-5}$ alkyl or straight $C_{2-4}$ alkyl substituted by hydroxy.

6. A method for suppressing the immune response of type 2 helper T cells in a patient comprising administering an effective amount of the pyrimidine compound or its pharmaceutically acceptable salt of claim 1 as an active ingredient to said patient.

7. A method for treating a patient with a disease wherein suppressing the immune response of type 2 helper T cells that are abnormally enhanced is necessary to overcome said disease, comprising administering an effective amount of the pyrimidine compound or its pharmaceutically acceptable salt of claim 1 to said patient.

8. The method of claim 7, wherein the disease is an allergic disease.

9. The method of claim 8, wherein the alleregic disease is asthma, allergic rinitis, or allergic dermatitis.

10. A method for enhancing the immune response of type 1 helper T cells in a patient comprising administering an effective amount of the pyrimidine compound or its pharmaceutically acceptable salt of claim 1 to a patient in need thereof.

11. A method for enhancing the production of IFNγ in a patient comprising administering an effective amount of the pyrimidine compound or its pharmaceutically acceptable salt of claim 1 to a patient in need thereof.

12. A method for treating a patient with a disease wherein enhancing the immune response of type 1 helper T cells is necessary to overcome said disease, comprising administering an effective amount of the pyrimidine compound or its pharmaceutically acceptable salt of claim 1 to said patient.

13. The method of claim 12, wherein the disease is viral or bacterial infectious disease.

* * * * *